(12) United States Patent
Detweiler et al.

(10) Patent No.: US 11,490,935 B2
(45) Date of Patent: Nov. 8, 2022

(54) ORTHOPAEDIC FIXATION DEVICES, SYSTEMS AND METHODS

(71) Applicant: Jace Medical, LLC, Warsaw, IN (US)

(72) Inventors: Jason F. Detweiler, Warsaw, IN (US); Scott Steffensmeier, Roanoke, IN (US)

(73) Assignee: Jace Medical, LLC, Warsaw, IN (US)

( * ) Notice: Subject to any disclaimer, the term of this patent is extended or adjusted under 35 U.S.C. 154(b) by 56 days.

(21) Appl. No.: 16/937,145

(22) Filed: Jul. 23, 2020

(65) Prior Publication Data

US 2020/0352617 A1 Nov. 12, 2020

Related U.S. Application Data

(62) Division of application No. 16/083,711, filed as application No. PCT/US2017/021501 on Mar. 9, 2017, now Pat. No. 10,758,290.

(60) Provisional application No. 62/306,937, filed on Mar. 11, 2016.

(51) Int. Cl.

| | |
|---|---|
| *A61B 17/80* | (2006.01) |
| *A61B 17/88* | (2006.01) |
| *A61B 17/84* | (2006.01) |
| *A61B 17/86* | (2006.01) |
| *A61B 17/17* | (2006.01) |
| *A61B 17/00* | (2006.01) |

(52) U.S. Cl.
CPC ...... *A61B 17/8076* (2013.01); *A61B 17/1728* (2013.01); *A61B 17/808* (2013.01); *A61B 17/8019* (2013.01); *A61B 17/8061* (2013.01); *A61B 17/842* (2013.01); *A61B 17/865* (2013.01); *A61B 17/8869* (2013.01); *A61B 17/8872* (2013.01); *A61B 17/8894* (2013.01); *A61B 2017/00407* (2013.01)

(58) Field of Classification Search
CPC .. A61B 17/80; A61B 17/8061; A61B 17/8076
See application file for complete search history.

(56) References Cited

U.S. PATENT DOCUMENTS

| | | | |
|---|---|---|---|
| 5,139,498 A * | 8/1992 | Astudillo Ley | A61B 17/8076 606/216 |
| 5,853,413 A | 12/1998 | Carter et al. | |
| 6,436,103 B1 | 8/2002 | Suddaby | |
| 7,022,141 B2 | 4/2006 | Dwyer et al. | |
| 7,052,499 B2 * | 5/2006 | Steger | A61B 17/8047 606/280 |
| 7,357,804 B2 | 4/2008 | Binder, Jr. et al. | |
| 7,473,255 B2 | 1/2009 | McGarity et al. | |
| 8,425,572 B2 * | 4/2013 | Grevious | A61B 17/8061 606/280 |
| 8,439,932 B2 | 5/2013 | Sheffer | |

(Continued)

*Primary Examiner* — Larry E Waggle, Jr.
(74) *Attorney, Agent, or Firm* — Schwegman Lundberg & Woessner, P.A.

(57) ABSTRACT

Implantable fixation devices for rejoining opposed portions of a separated bone. The devices include plates that may be affixed to a rib and realign separated portions of the rib or other body part. The devices may also include various locking mechanisms that receive a cable that may be used to realign and bring together separated portions of a bone or other body part. The devices may further include plates that may be affixed to a sternum and realign separated portions of the sternum or other body part.

20 Claims, 24 Drawing Sheets

(56) References Cited

U.S. PATENT DOCUMENTS

| | | | |
|---|---|---|---|
| 8,460,345 B2* | 6/2013 | Steger | A61B 17/80 606/280 |
| 8,535,355 B2* | 9/2013 | Prasad | A61B 17/8014 606/291 |
| 8,808,334 B2 | 8/2014 | Strnad et al. | |
| 9,283,008 B2* | 3/2016 | Gonzalez-Hernandez | A61B 17/80 |
| 2003/0045880 A1 | 3/2003 | Michelson | |
| 2004/0102775 A1 | 5/2004 | Huebner | |
| 2006/0173459 A1 | 8/2006 | Kay et al. | |
| 2016/0051297 A1 | 2/2016 | Steflensmeier | |

* cited by examiner

ORTHOPAEDIC FIXATION DEVICES, SYSTEMS AND METHODS

CROSS REFERENCES TO RELATED APPLICATIONS

This is a division of U.S. non-provisional patent application Ser. No. 16/083,711, entitled, Orthopaedic Fixation Devices, Systems and Methods, filed Sep. 10, 2018, which is incorporated herein by reference. U.S. non-provisional patent application Ser. No. 16/083,711 claims the benefit of U.S. Provisional Patent Application Ser. No. 62/306,937, entitled Orthopaedic Fixation Devices, Systems and Methods, filed Mar. 11, 2016, which is incorporated herein by reference.

FIELD

The present disclosure relates generally to orthopaedic fixation devices, systems and methods of such fixation. More particularly the present disclosure relates to the use of in bone fixation where adjacent sections of a bone are intended to be rejoined, for example, a bone that has been cut, broke, resected, or otherwise is in need of repair.

BACKGROUND

In some surgical procedures involving bones, for instance, the procedure may involve separating a bone into portions, which are thereafter reunited. This happens, for instance, in entries into the chest cavity, as for heart surgery, where the sternum is required to be separated along its length (resected), in the transverse plane, or a combination of the two. There may be other instances where a bone has been separated for the purpose of surgery or has undergone fracturing through some trauma, and is thereafter to have portions rejoined for proper healing.

SUMMARY

The present disclosure describes various implantable fixation devices for rejoining opposed portions of a separated bone or other body part. The devices include plates that may be affixed to a rib and used to realign separated portions of the rib or other body part. The devices may also include various cable locking mechanisms and anchors that receive a cable and may be used to realign and bring together separated portions of a bone or other body part. The devices further include plates that may be affixed to a sternum and used to realign separated portions of the sternum or other body part.

BRIEF DESCRIPTION OF THE DRAWINGS

Embodiments of devices, systems, and methods are illustrated in the figures of the accompanying drawings which are meant to be exemplary and not limiting, in which like references are intended to refer to like or corresponding parts, and in which.

DETAILED DESCRIPTION

While the embodiments described herein are in the environment of an orthopaedic fixation device, system and method for use on the sternum, in particular, it should be appreciated that the disclosure has broader application. That could be, for instance, such as where bone or other body parts having suitable rigidity require closure or other relational organization, such as joining two opposing anatomical structures. This could be in the context of a traumatic break or other unintended separation, or as part of a surgical procedure. Thus, the present disclosure can have usefulness in contexts beyond fixation of bones which have been resected in surgery. Further, it should be appreciated that aspects of the disclosure described herein may be applicable to other body parts, including muscles, tendons, etc.

In general, the present disclosure relates to implantable fixation devices for rejoining opposed portions of a separated bone. Implantable is used in the sense that it is sub-cutaneous, but it is possible that applications leaving the fixation device external could be envisioned.

Figure 1:
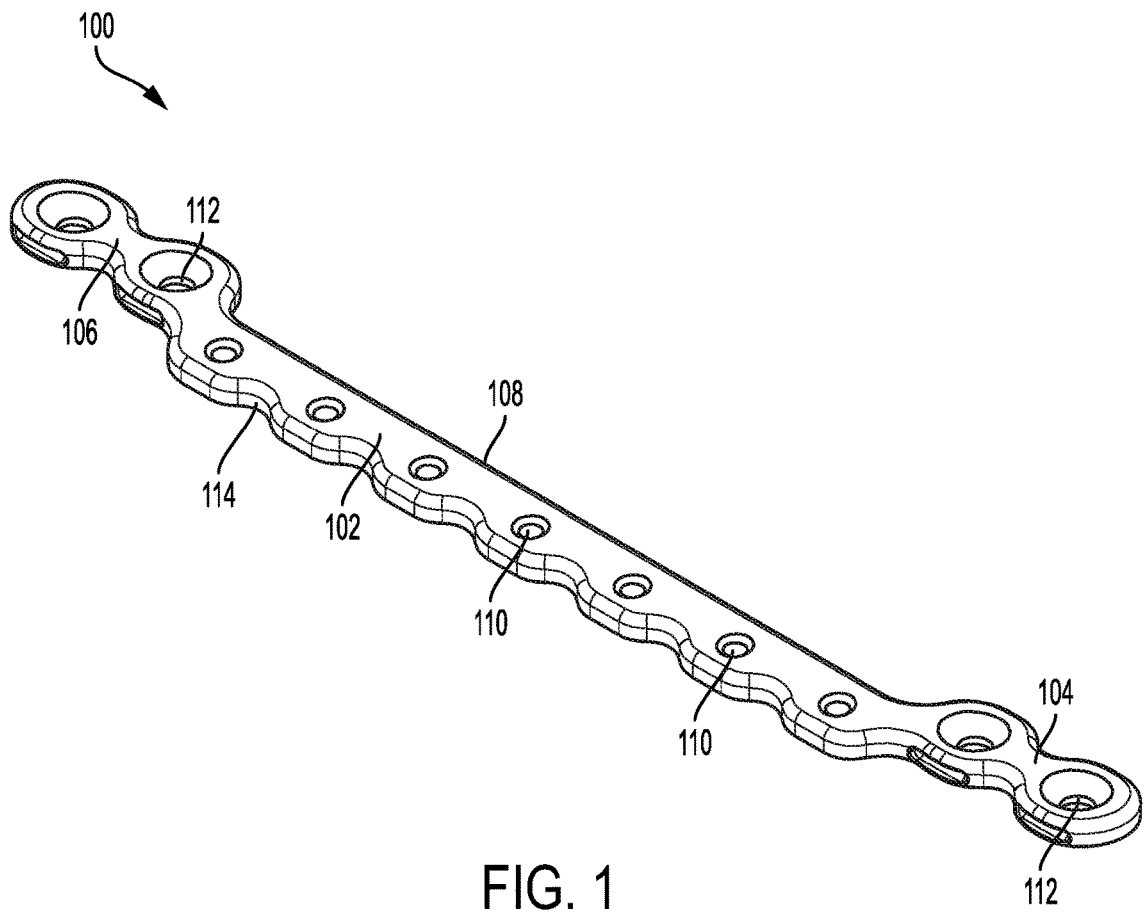
FIG. 1 illustrates a perspective view of an implantable fixation device according to an embodiment of the disclosure.
Figure 2:
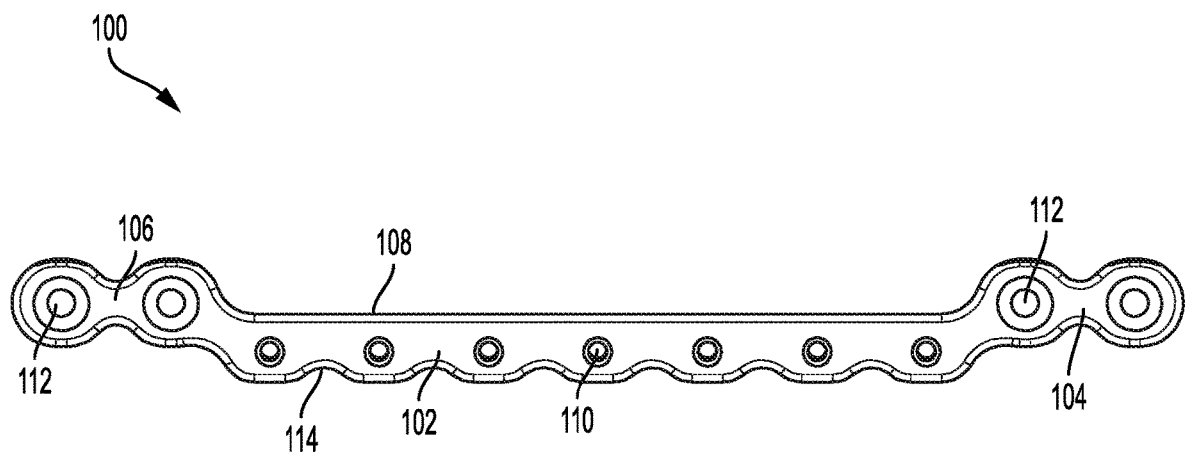
FIG. 2 illustrates a top view of the implantable fixation device of FIG. 1 according to the disclosure.

FIGS. 1-2 illustrate an implantable fixation device 100 in the form of a plate according to an embodiment of the disclosure. As illustrated in FIGS. 1 and 2, the fixation device 100 includes a first portion 102 that extends in a longitudinal direction, a second portion 104 extending from a first end of the first portion 102, and a third portion 106 extending from a second end (opposite the first end) of the first portion 102.

The first portion 102 includes a first edge 108. The second portion 104 and the third portion 106 extend in opposite directions away from the first and second ends, respectively, of the first portion 102, and are offset with respect to the first portion 102. This offset forms a substantially "U" shape with the first edge 108 forming a bottom portion of the "U" shape, and respective edges of the second portion 104 and the third portion 106 forming right and left portions of the "U" shape.

The first portion 102 may also include one or more apertures 110. The apertures 110 may be configured to receive suture material for use in suturing two separated portions of bone together for healing. The apertures 110 may alternatively be configured to receive fasteners or other fastening mechanisms. The second portion 104 and the third portion 106 may each include one or more fastener apertures 112. The fastener apertures 112 may be configured to receive fasteners (such as screws, pins, rivets, or other types of fasteners, etc.) for coupling the fixation device 100 to a bone.

As illustrated, the first edge 108 of the first portion 102 is substantially straight. This may provide a guiding surface for a cutting instrument or tool when the fixation device 100 is placed on a bone prior to separation of the bone. The first portion 102 includes a second edge 114 that is non-straight (e.g., includes one or more peaks and valleys). The peaks and valleys of the second edge 114 may assist in retaining a suture material (or other fastening mechanism) when the fixation device 100 is in use. However, the first edge 108 and/or the second edge 114 may be substantially straight or have any other shape or geometry. For example, the first edge 108 is illustrated as non-straight in FIG. 4.

The fixation device 100 may be used to realign and place two separated portions of bone together for healing. The fixation device 100 may be coupled to the bone prior to separation of the bone or after separation of the bone has occurred.

Figure 3:
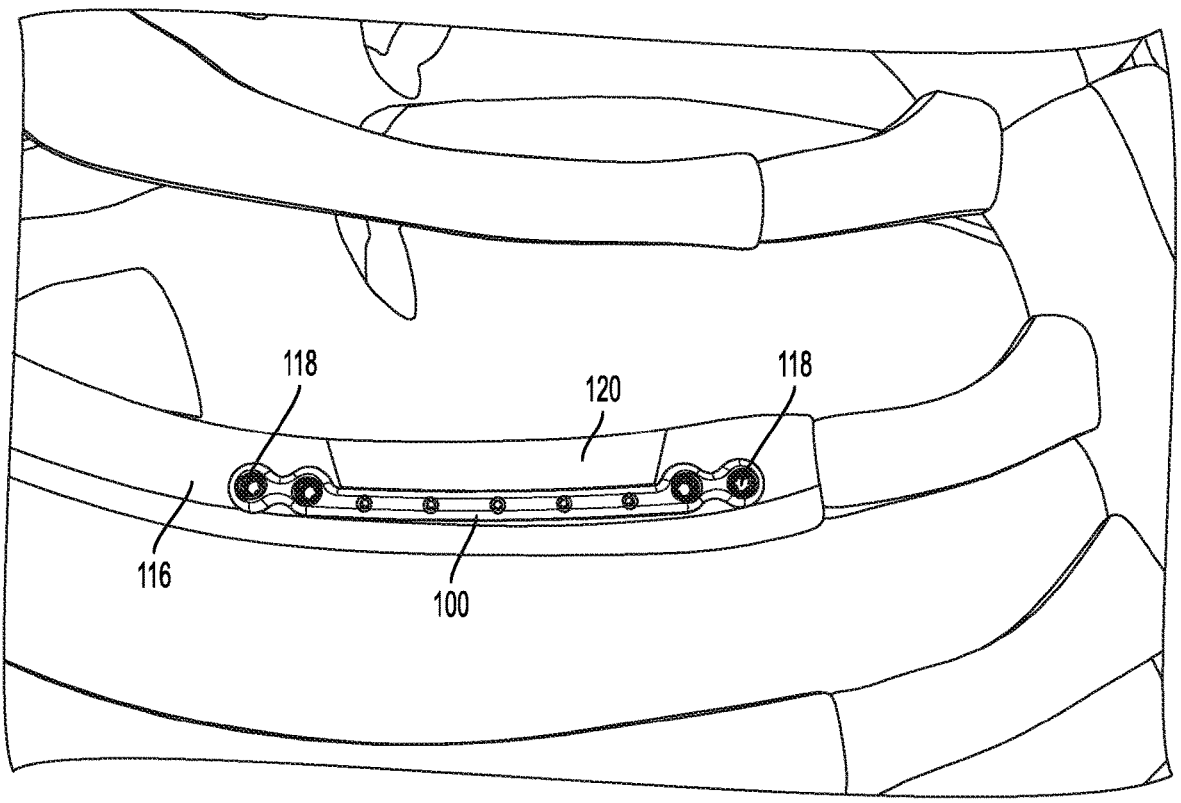
FIGS. 3 and 4 illustrate perspective views of the implantable fixation device of FIG. 1 affixed to a bone according to the disclosure.

In an example, the fixation device 100 may be coupled to a rib 116, as illustrated in FIG. 3. In this respect, the fixation device 100 may be contoured to the geometry of the rib 116 and fastened to the rib 116 by inserting fasteners 118 into the fastener apertures 112 (illustrated in FIGS. 1 and 2). One or more suture apertures may also be created in the rib 116 using a drilling tool or other instrument, and using the apertures 110 (illustrated in FIGS. 1 and 2) as guides.

When the rib 116 is separated forming fragment 120 prior to the placement of the fixation device 100, the fasteners 118 may be inserted into the main portion of the rib 116 (as opposed to the fragment 120). However, it should be appreciated that the fasteners 118 may be inserted into the fragment 120 instead of or in addition to the main portion of the rib 116. When the fixation device 100 is placed on the rib 116 prior to the fragment 120 being created (pre-resection), the first edge 108 (illustrated in FIGS. 1 and 2) may be used as a guide for a cutting tool to create the fragment 120. The fragment 120 may then be removed and a surgical procedure performed. For example, the fragment 120 may be removed to provide for access into the body, and allow for a surgical procedure to be performed.

Figure 4:
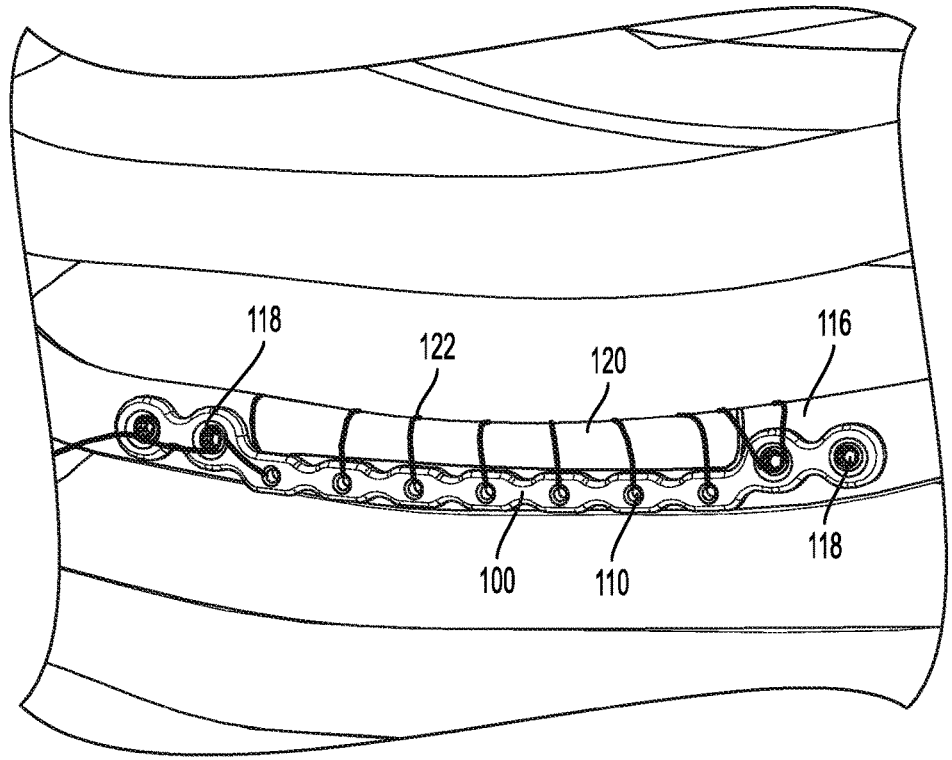

Referring to FIG. 4, after the procedure, the fragment 120 is repositioned and aligned with the main portion of the rib 116. One or more sutures may be installed by threading one or more suture portions 122 through the apertures 110 (illustrated in FIGS. 1 and 2) and corresponding apertures in the rib 116 and extending the suture portion(s) 122 around the fragment 120. The suture portion(s) 122 hold the fragment 120 in alignment with the rib 116 to allow the rib 116 and fragment 120 to heal. While the suture portion(s) 122 are illustrated in FIG. 4 as a single suture portion 122 that is wrapped around the fragment, the suture portion(s) 122 may include separate suture portions that are tied off or otherwise secured at each aperture 110 (illustrated in FIGS. 1 and 2). Further, while the suture portion(s) 122 are illustrated in FIG. 4 as being secured at each end using fasteners 118, other means of securing the suture portion(s) 122 may be used, including one or more of the embodiments described below.

It should be appreciated that the size of the fixation device 100 may be adapted for the particular use. For example, the length of the first portion 102, number of apertures 110, length of the respective second portion 104 and third portion 106, and number of apertures 112 may be increased or decreased as desired.

Figure 5:
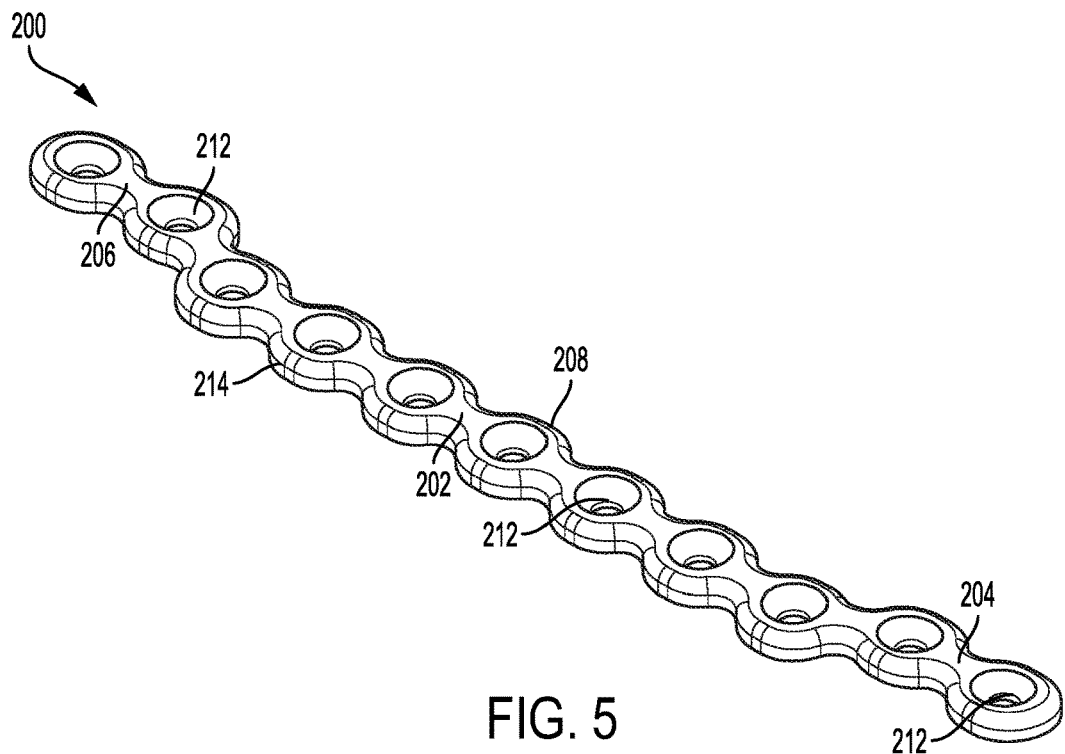
FIG. 5 illustrates a perspective view of another implantable fixation device according to an embodiment of the disclosure.
Figure 6:
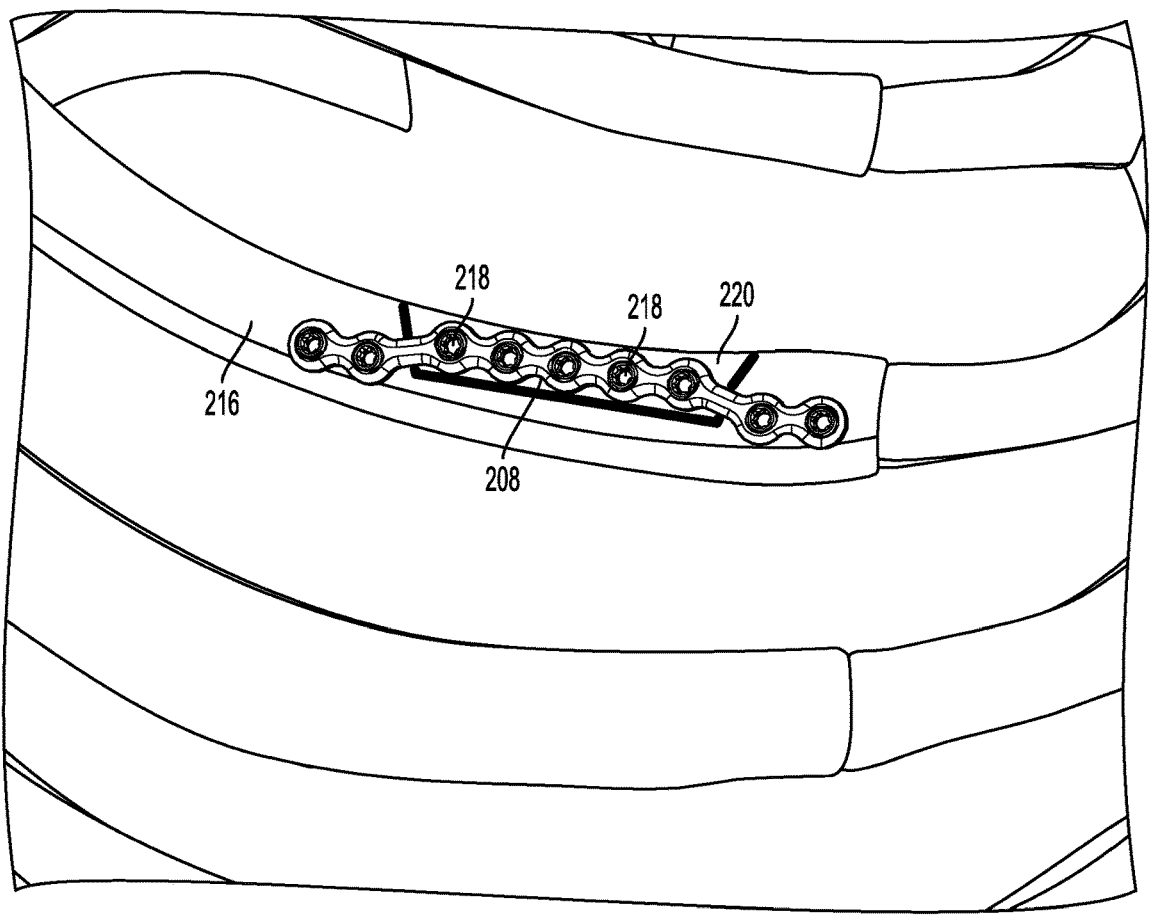
FIG. 6 illustrates a perspective view of the implantable fixation device of FIG. 5 affixed to a bone according to the disclosure.

FIGS. 5 and 6 illustrate another implantable fixation device 200 in the form of a plate according to an embodiment of the disclosure. As illustrated, the fixation device 200 includes a first portion 202 that extends in a longitudinal direction, a second portion 204 extending from a first end of the first portion 202, and a third portion 206 extending from a second end (opposite the first end) of the first portion 202.

The first portion 202 includes a first edge 208. The second portion 204 and the third portion 206 extend in opposite directions away from the first and second ends, respectively, of the first portion 202, and are offset with respect to the first portion 202. This offset forms a substantially "U" shape with the first edge 208 forming a bottom portion of the "U" shape, and respective edges of the second portion 204 and the third portion 206 forming right and left portions of the "U" shape.

In this embodiment, the first portion 202 includes one or more fastener apertures 212. Similarly, the second portion 204 and the third portion 206 each include one or more fastener apertures 212. As described above, the fastener apertures 212 may be configured to receive fasteners (such as screws, pins, rivets, or other types of fasteners, etc.) for coupling the fixation device 200 to a bone.

As illustrated, the first edge 208 of the first portion 202 is non-straight (e.g., includes one or more peaks and valleys). The first portion 202 may also include a second edge 214 that is non-straight. However, the first edge 208 and/or the second edge 214 may be substantially straight or have any other shape or geometry. For example, the first edge 208 may be substantially straight. This may provide a guiding surface for a cutting instrument or tool when the fixation device 200 is placed on a bone prior to separation of the bone.

As with the fixation device 100, the fixation device 200 may be used to realign and place two separated portions of bone together for healing. The fixation device 200 may be coupled to the bone prior to separation of the bone or after separation of the bone has occurred.

In an example, the fixation device 200 may be coupled to a rib 216, as illustrated in FIG. 6. In this respect, the fixation device 200 may be contoured to the geometry of the rib 216 and fastened to the rib 216 by inserting fasteners 218 into the fastener apertures 212 of the first portion 202. The rib 216 may then be separated forming fragment 220. The first edge 208 may be used as a guide for a cutting tool to create the fragment 220. The fragment 220 may then be removed along with the fixation device 200 and a surgical procedure performed.

After the procedure, the fragment 220 with the fixation device 200 coupled thereto is repositioned and aligned with the main portion of the rib 216. One or more additional fasteners 218 may then be installed through the respective fastener apertures 212 of the second portion 204 and the third portion 206 to hold the fragment 220 in alignment with the rib 216 to allow the rib 216 and fragment 220 to heal.

Like the fixation device 100, it should be appreciated that the size of the fixation device 200 may be adapted for the particular use. For example, the length of the first portion 202, length of the respective second portion 204 and third portion 206, and number of apertures 112 may be increased or decreased as desired.

Figure 7:
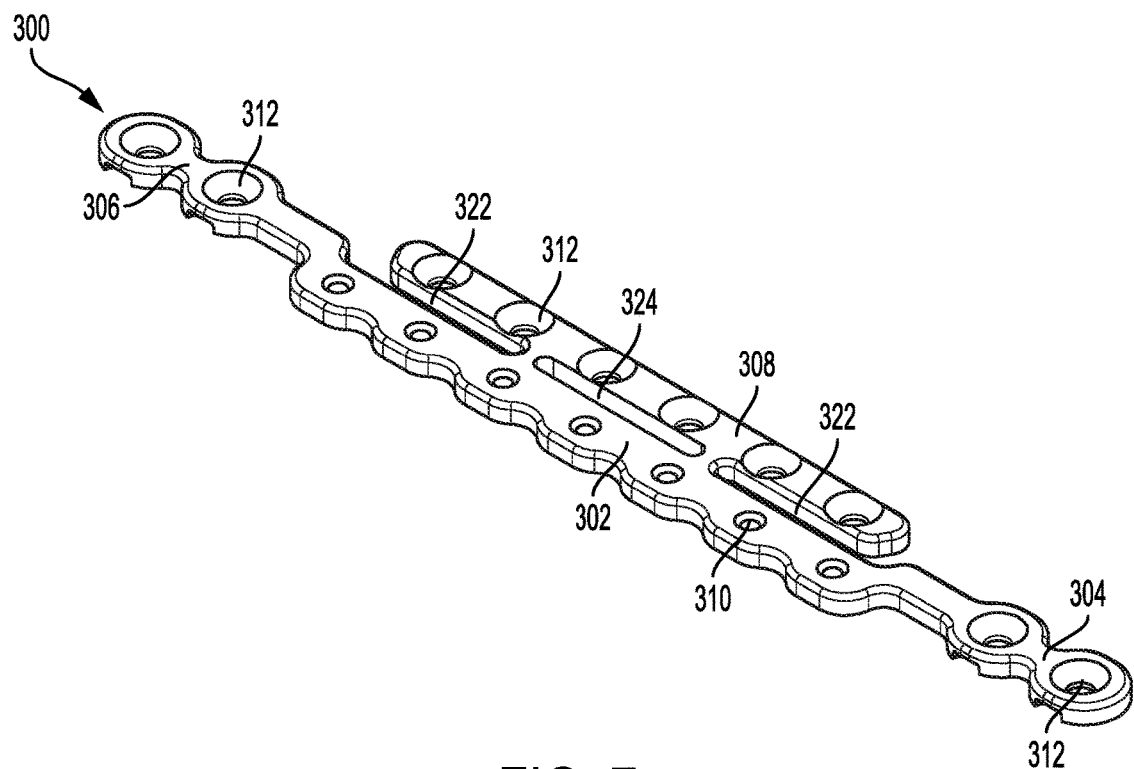
FIG. 7 illustrates a perspective view of another implantable fixation device according to an embodiment of the disclosure.
Figure 8:
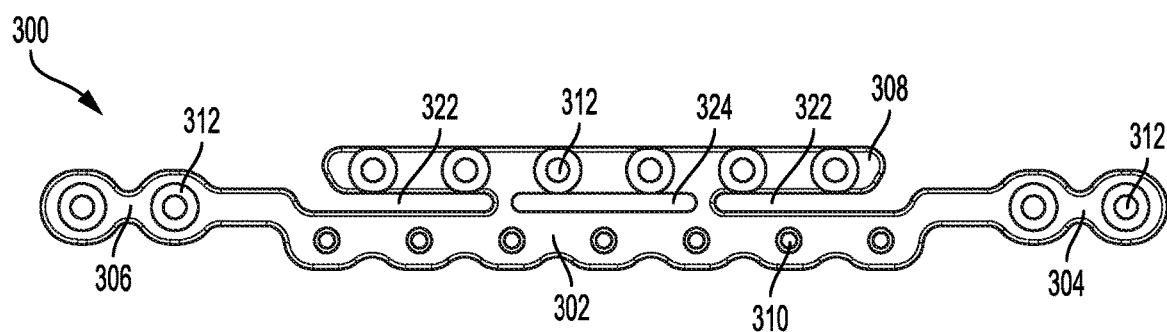
FIG. 8 illustrates a top view of the implantable fixation device of FIG. 7 according to the disclosure.
Figure 9:
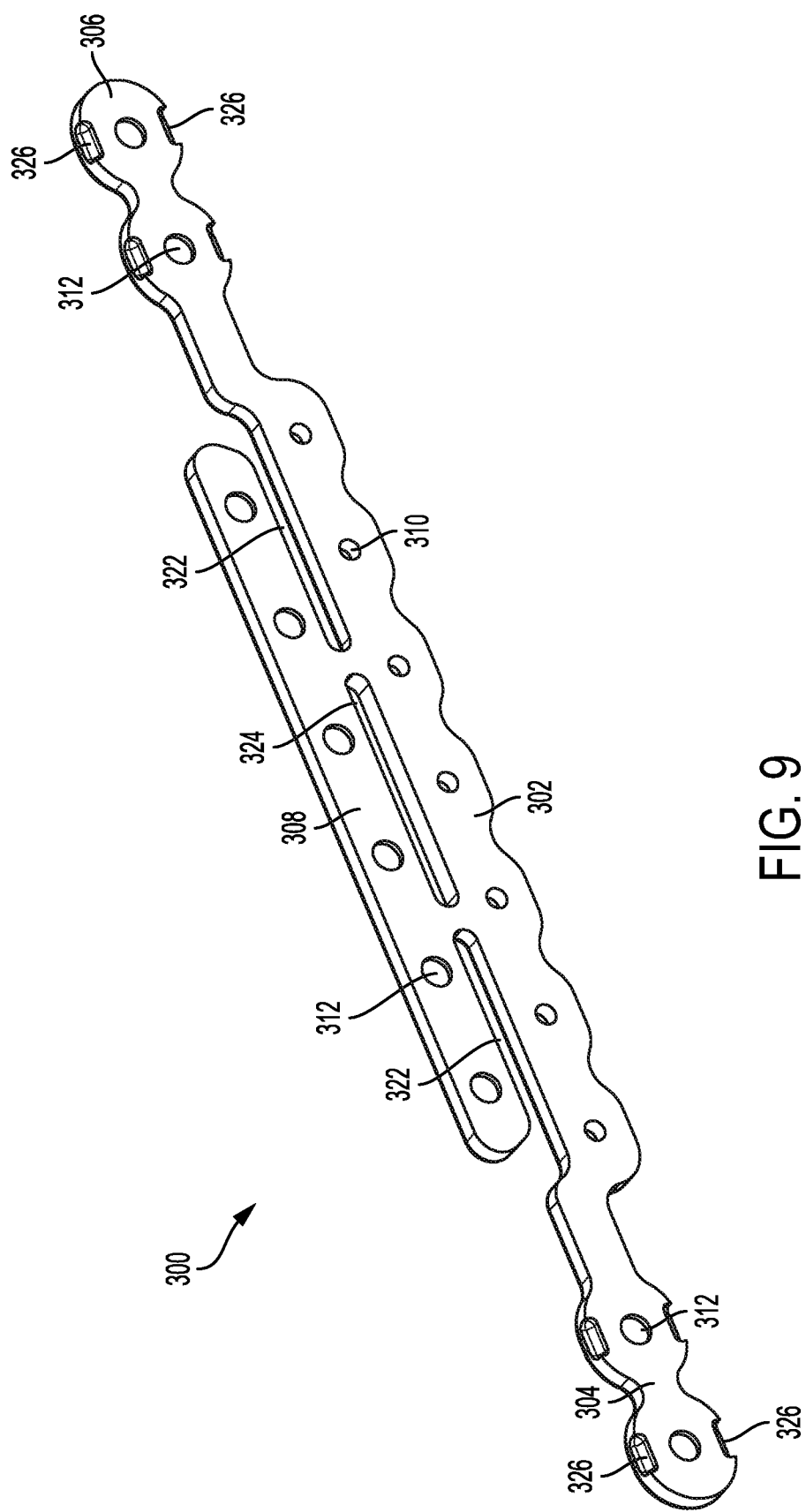
FIG. 9 illustrates a perspective bottom view of the implantable fixation device of FIG. 7 according to the disclosure.

FIGS. 7-9 illustrate another implantable fixation device 300 in the form of a plate according to an embodiment of the disclosure. As illustrated, the fixation device 300 is a type of combination of the fixation devices 100 and 200. The fixation device 300 includes a first portion 302 that extends in a longitudinal direction, a second portion 304 extending from a first end of the first portion 302, a third portion 306 extending from a second end (opposite the first end) of the first portion 302, and a fourth portion 308 (similar to the portion 202 of the fixation device 200).

The second portion 304 and the third portion 306 extend in opposite directions away from the first and second ends, respectively, of the first portion 302, and are offset with respect to the first portion 302. This offset forms a substantially "U" shape with a first edge of the first portion 302 forming a bottom portion of the "U" shape, and respective edges of the second portion 304 and the third portion 306 forming right and left portions of the "U" shape.

The first portion 302 includes one or more apertures 310. The apertures 310 may be configured to receive suture material for use in suturing two separated portions of bone together for healing, as described above with respect to FIG. 1. The apertures 310 may alternatively be configured to receive fasteners or other fastening mechanisms. The second portion 304 and the third portion 306 each include one or more fastener apertures 312, as described above with respect to FIG. 1.

The fourth portion 308 (which is similar to the portion 202 of the fixation device 200) also includes one or more fastener apertures 312, as described above with respect to FIG. 2. However, the fourth portion 308 is coupled to the first portion 302 and oriented longitudinally substantially between the second portion 304 and the third portion 306. The orientation of the fourth portion 308 with respect to the first portion 302 form channels 322 and 324. The channels 322 and 324 may provide a guiding surface for a cutting instrument or tool when the fixation device 300 is placed on a bone prior to separation of the bone.

The fixation device 300 may be used to realign and place two separated portions of bone together for healing. The fixation device 300 may be coupled to the bone prior to separation of the bone or after separation of the bone has occurred.

In an example, the fixation device 300 may be coupled to a rib. In this respect, the fixation device 300 may be contoured to the geometry of the rib and fastened to the rib by inserting fasteners into the fastener apertures 312 of the fourth portion 308. One or more suture apertures or fastener apertures may also be created in the rib using a drilling tool or other instrument, and using the apertures 310 as guides.

The channels 322 and 324 may be used as a guide for a cutting tool to create a fragment (such as fragment 120 illustrated in FIG. 3). The fragment may then be removed, along with the fixation device 300 (because the fixation device 300 is fastened to the fragment using the fastener apertures 312 of the fourth portion 308), and a surgical procedure performed. After the procedure, the fragment is repositioned and aligned with the main portion of the rib. One or more fasteners are then inserted into the fastener apertures 312 of the second portion 304 and the third portion 306, respectively. One or more sutures may also be installed by threading one or more suture portions through the apertures 310, in a similar manner as described above with respect to FIG. 4.

It should be appreciated that the size of the fixation device 300 may be adapted for the particular use. For example, the length of the first portion 302, number of apertures 310, length of the respective second portion 304, third portion 306 and fourth portion 308, and number of apertures 312 may be increased or decreased as desired.

Referring again to FIG. 9, any of the fixation devices described herein may include recesses or other mating features, similar to recesses 326. The recesses 326 (or other mating feature) may be configured to receive corresponding members of an implant positioning device, described in further detail below.

FIGS. 10-17 illustrate an implant positioning device 400 according to an embodiment of the disclosure. As illustrated, the positioning device 400 includes a fastener guide 402, a fastener loading mechanism 404 coupled to the fastener guide 402, and a compression attachment mechanism 406.

Figure 14:
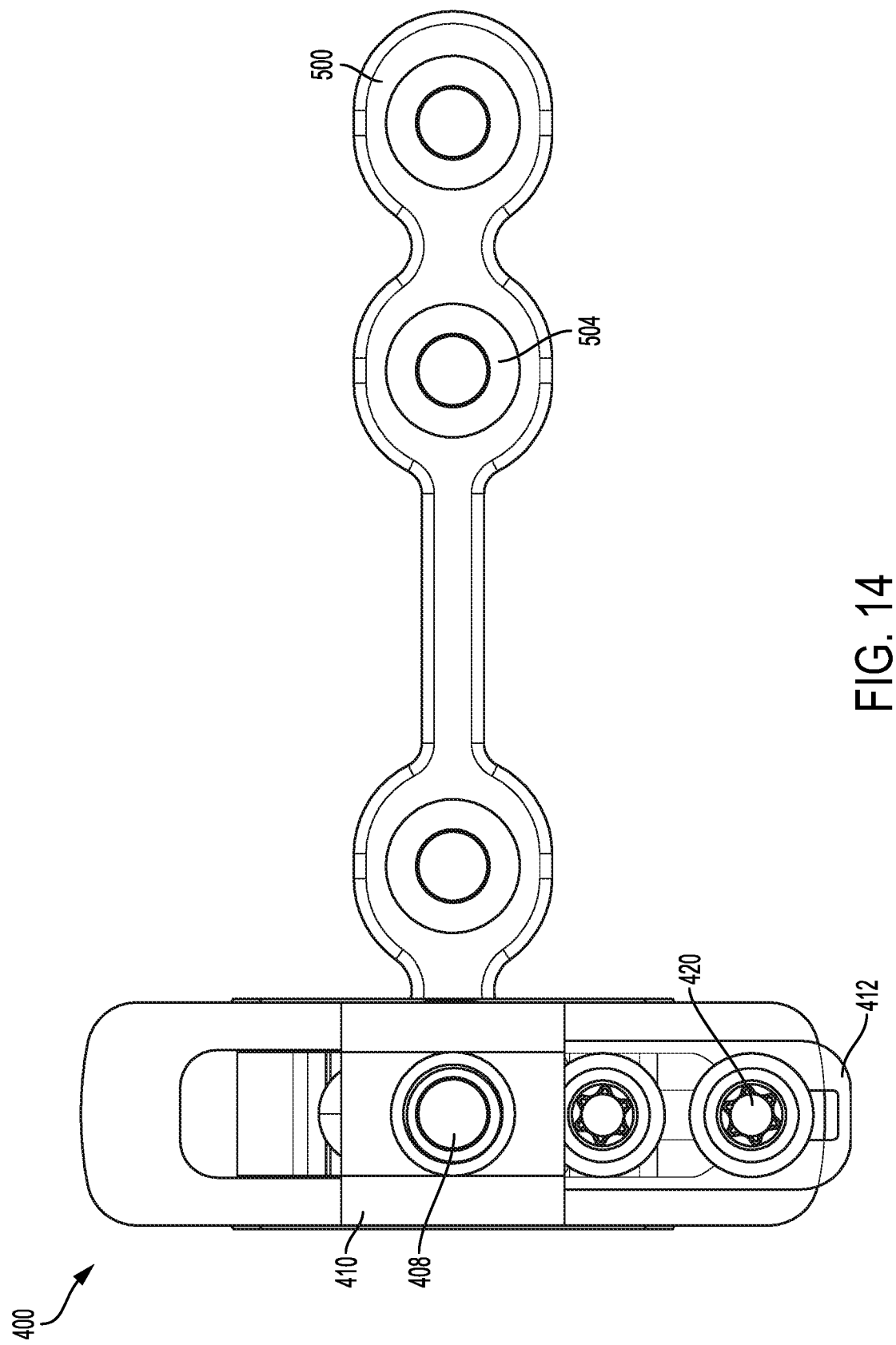
FIG. 14 illustrates a top view of the implant positioning device of FIG. 10 according to the disclosure.
Figure 15:
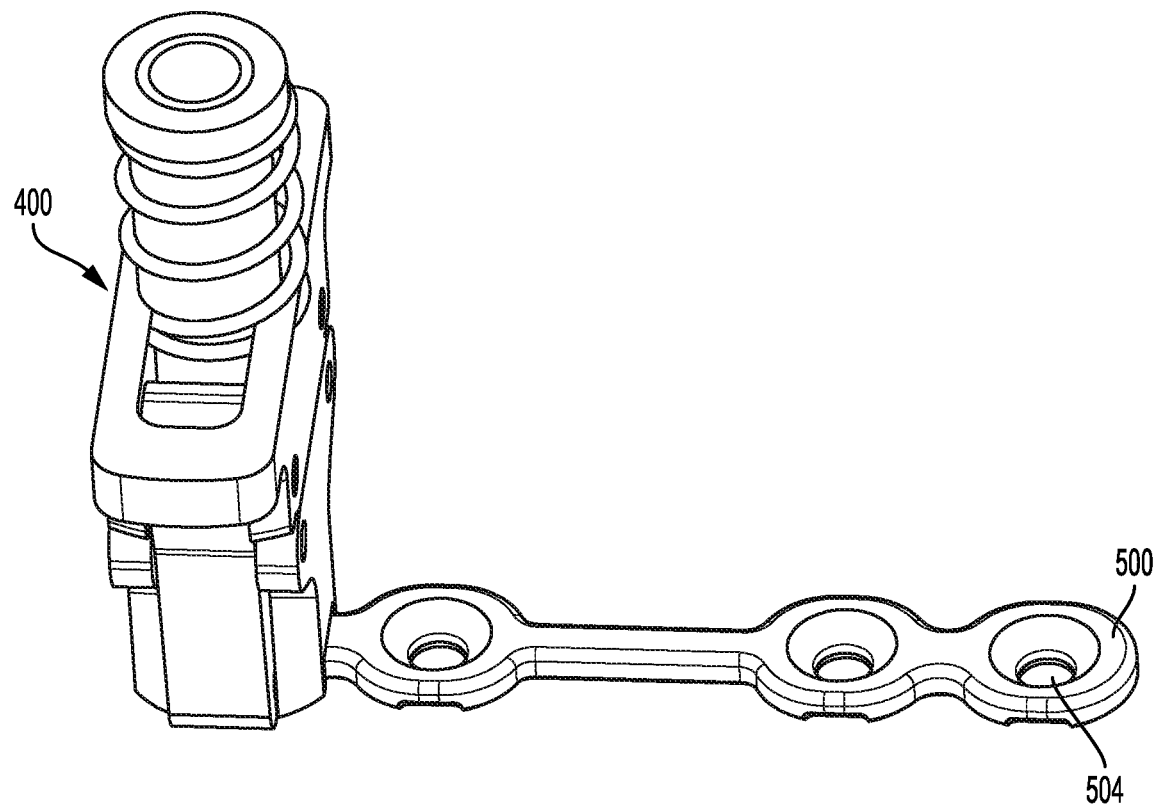
FIG. 15 illustrates a perspective view of the implant positioning device of FIG. 10 coupled to a plate according to the disclosure.

The fastener guide 402 includes an aperture 408 (as best illustrated in FIG. 14) extending through the fastener guide 402. As illustrated, the fastener guide 402 is in the form of a hollow tubular member. However, it should be appreciated that the fastener guide 402 may take the form of other shapes. The fastener guide 402 may be used to guide a fastener being driven into a fastener aperture of an implantable fixation device (such as a plate) to fasten the plate to a bone, calcaneus body part, or other area of a patient. The fastener guide 402 may also be used to guide a driver and/or drill depending on the application. The fastener guide 402 may also be used to guide other instruments, for example, to place markings, pegs, headless pins, etc. in a bone, which then serve as locating features to place plates or any other device.

Figure 10:
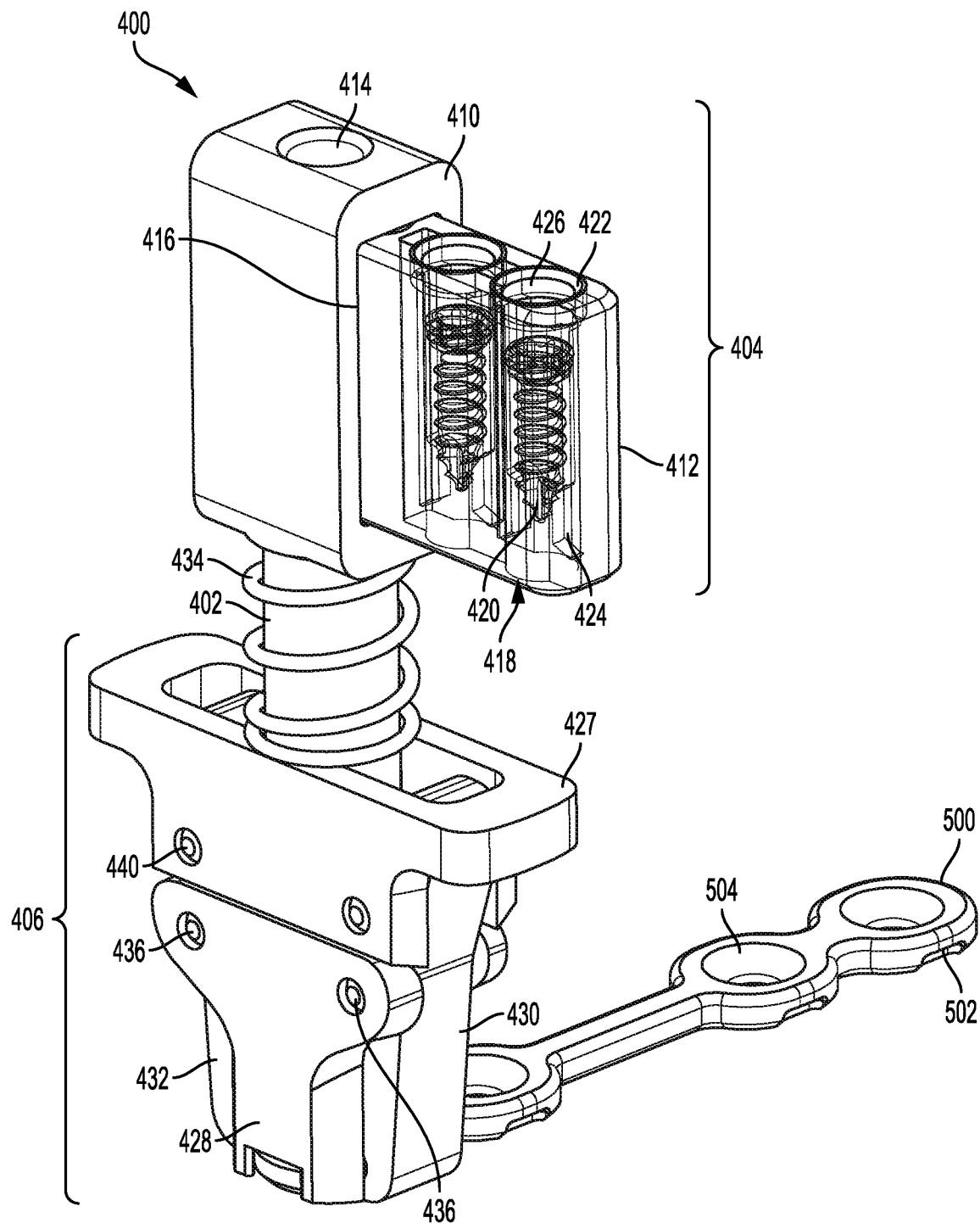
FIG. 10 illustrates a perspective view of an implant positioning device according to an embodiment of the disclosure.

The loading mechanism 404 includes a body portion 410 and a fastener holder 412. The body portion 410 is coupled to the fastener guide 402 at a first end (the top end as illustrated in FIG. 10). The body portion 410 includes a first aperture 414 extending longitudinally through the body portion 410 that aligns with the aperture 408 of the fastener guide 402. The body portion 410 also includes a second aperture 416 extending through the body portion 410 perpendicular to a longitudinal axis of the body portion 410 and configured to receive the fastener holder 412.

As illustrated, the fastener holder 412 (illustrated in phantom in FIG. 10 to show internal components) is configured to be received within the second aperture 416. The fastener holder 412 includes one or more apertures 418 (as illustrated there are three apertures 418, however there may be more or less), each configured to receive and hold a fastener (such as fastener 420. Each aperture 418 may also include a fastener captive element 422. The fastener captive element 422 retains the fastener 420 in the respective apertures 418.

The fastener captive element 422 may be spring elements that creates tension against the fastener 420 (for example, the threads of the fastener 420) and centers the fastener 420 in the respective aperture 418. As illustrated, the fastener captive element 422 includes three spring elements or prongs 424 extending downwardly from an upper collar 426. The prongs 424 include teeth that contact and grip a side of the fastener 420 (such as the threads of the fastener 420), and the collar 426 surrounds a head of the fastener 420 to hold the fastener 420 in the fastener captive element 422. However, it should be appreciated that more or less than three prongs 424 may be used, and the fastener captive element 422 may be a cage, or other structure capable of retaining a fastener within a respective aperture 418.

The prongs 424 may be located at various positions around each respective collar 426, for example, about 120 degrees apart, when there are three prongs 424. As illustrated, the fastener captive element 422 centers the fasteners 420 in the respective aperture 418 to ensure the fastener 420 is appropriately deployed through the fastener guide 402 when the respective aperture 418 is aligned with the aperture 408 of the fastener guide 402.

The fastener captive element 422 serves as a capture mechanism. For example, the fastener captive element 422 is biased to compress against and apply a force to the fastener 420 and hold the fasteners 420 within the respective aperture 418 of the fastener holder 412. Each fastener captive element 422 may be disposed in and optionally removable from the respective aperture 418 for ease of loading fasteners into the fastener holder 412. For example, a fastener, such as fastener 420, may be disposed in a fastener captive element 422 and then the fastener captive element 422 along with the fastener 420 may be loaded into a corresponding aperture 418. In this respect, the apertures 418 may respectively include shoulders that receive and abut the collar 426 of the respective fastener captive element 422 and prevent the fastener captive element 422 from sliding or being forced out of the fastener holder 412 when the fastener 420 is driven into a bone or other body part.

As a fastener 420 is driven into a bone or other material, the fastener captive element 422 may expand elastically as a head of the fastener having a larger diameter than a shank or threaded portion of the fastener passes through the respective aperture 418. Each of the fasteners 420 may have a head portion having a feature that mates with a driver (for example, a flat head, cross head, hex head etc. of a driver and/or drill) for use in insertion and receiving torque to drive the fasteners 420 into a bone or other body part. The fastener captive element 420 then returns to a normal resting state for repeated use. The fastener captive element 420 also holds the fastener 420 within the respective aperture 418 and prevents the fasteners 420 from accidentally falling out of the aperture 418 onto an operating room floor or into a patient's open body cavity.

The fastener holder 412 and the body portion 410 may also include corresponding tactile indicators that provide a tactile feel to a user when each respective aperture 418 is aligned with the aperture 408 of the fastener guide 402 as the fastener holder 412 is moved through the aperture 416 of the body portion 410. This provides confirmation to the user that the aperture 418 (an a fastener 420 held therein) is appropriately aligned and can be driven into a bone or other body part.

The fastener holder 412 may also hold differing types of fasteners at the same time in respective apertures 418. This allows a user to select the appropriate fastener for the particular application. In an aspect, the fastener holder 412 may be disposable, and pre-loaded with fasteners. For example, the fastener holder 412 may be removable from the body portion 410 allowing the fastener holder 412 to be easily replaced during a surgical procedure. The fastener holder 412 also allows for drilling and depth measuring and may hold multiple different fasteners with differing lengths.

The compression attachment mechanism 406 may include a first portion 427, a second portion 428, and first and second pivot members 430,432 respectively. The first portion 427 may be disposed around the fastener guide 402 and slidable along a longitudinal axis of the fastener guide 402. The second portion 428 may be coupled to a second end of the fastener guide 402 opposite the end of the fastener guide 402 that the body portion 410 is positioned. The first portion 427 may also be spring biased in a direction toward the second portion 428 by a bias member 434 (such as a spring). As illustrated, the bias member 434 is disposed around the fastener guide 402 between the body portion 410 and the first portion 427.

The respective first and second pivot members 430,432 may be pivotally coupled to the second portion 428 and be oriented on opposing sides of the fastener guide 402. For example, the first and second pivot members 430,432 may be pivotally coupled to the second portion 428 by pins 436, or other mechanism for providing the pivot coupling.

Figure 11:
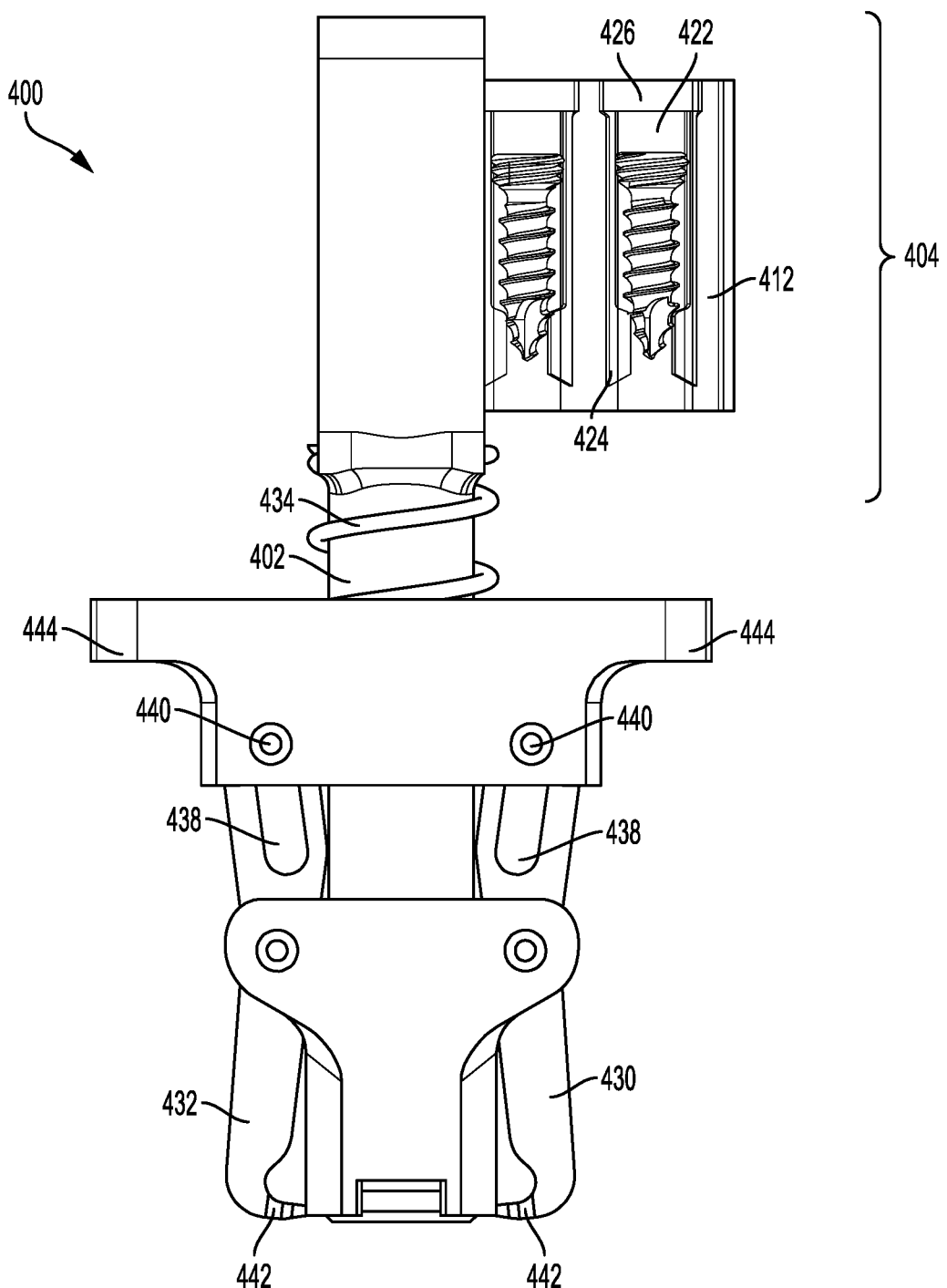
FIG. 11 illustrates a side view of the implant positioning device of FIG. 10 according to the disclosure.
Figure 13:
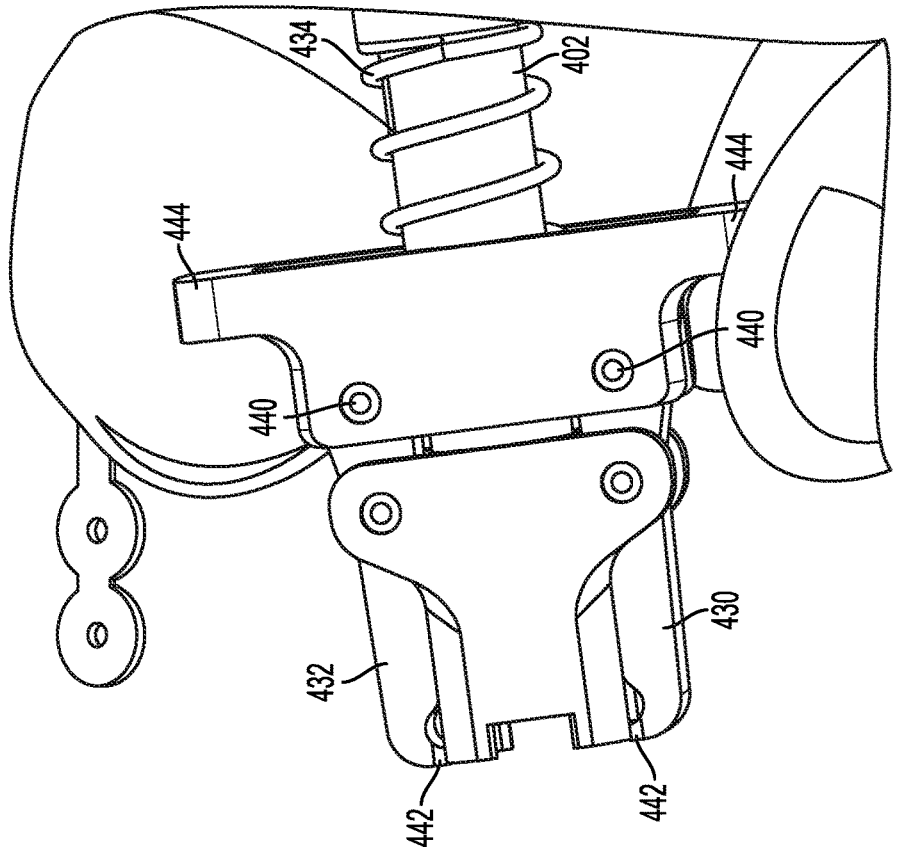
FIG. 13 illustrates the implant positioning device of FIG. 10 in a closed position according to the disclosure.

Referring to FIG. 11, the respective first and second pivot members 430,432 may include elongated apertures 438, and pins 440 may be disposed through the apertures 438 to couple the respective first and second pivot members 430, 432 to the first portion 427.

The respective first and second pivot members 430,432 may also include gripping members 442 on ends of the respective first and second pivot members 430,432 that project inward toward the fastener guide 402. The gripping members 442 may be used to grip an implantable fixation device, such as a plate. To align the fastener guide 402 with a fastener aperture in the plate to install a fastener through the fastener aperture in the plate and couple the plate to a bone, calcaneus body part, or other area of a patient.

The positioning device 400 may be releasably coupled to an implantable fixation device, such as a plate, by manipulating the compression mechanism 406. For example, the respective first and second pivot members 430,432, and the respective gripping members 442 may be moved between an open position (or loading position) allowing a plate to be placed between the gripping members 442 and a closed position in which the gripping members 442 grip the plate.

Figure 12:
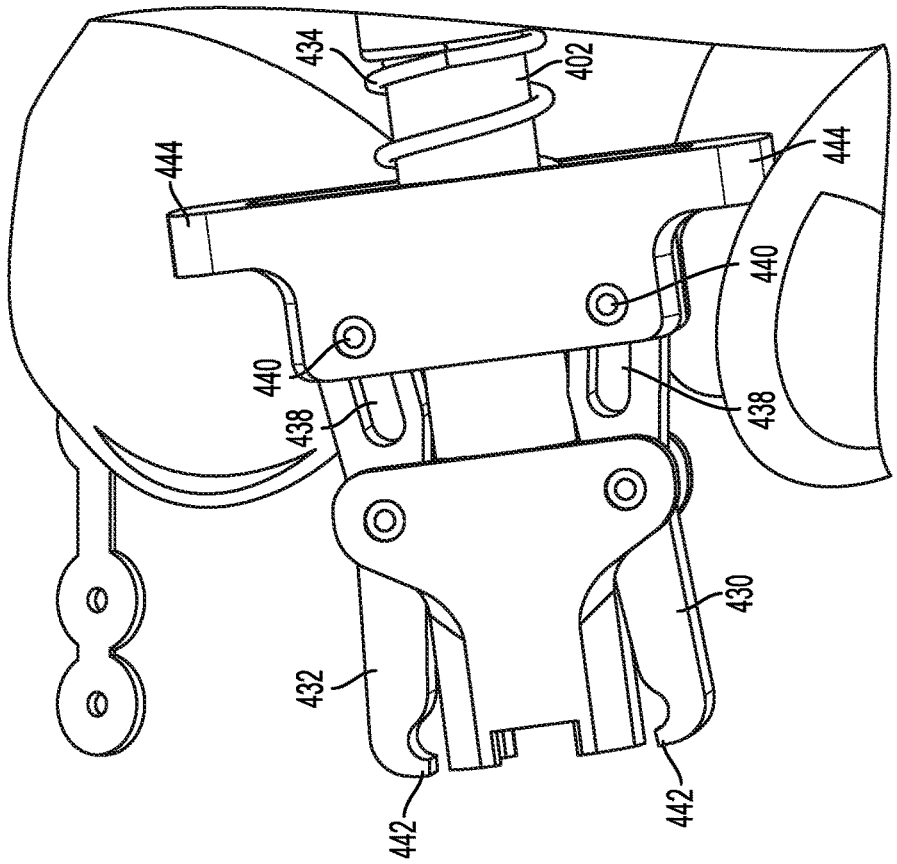
FIG. 12 illustrates the implant positioning device of FIG. 10 in an open position according to the disclosure.

Referring to FIGS. 11 and 12, handle portions 444 of the first portion 427 may be used to slide the first portion 427 in a direction towards the loading mechanism 404 and thereby compress the bias member 434. As the first portion 427 slides towards the loading mechanism 404, the pins 440 slide along the elongated apertures 438 is a same direction causing the respective first and second pivot members 430,432 to pivot and the gripping members 442 of the respective first and second pivot members 430,432 to move away from the fastener guide 402 to the open position.

In the open position, a plate 500 (illustrated in FIG. 10) may be inserted between the gripping members 442. In an aspect, the plate 500 may include recesses 502 (similar to the recesses 326 described above). The recesses 502 are configured to mate with and receive the gripping members 442 when the gripping members 442 are in the closed position.

To move the gripping members 442 to the closed position, the use releases the compression force of the bias member 434 by allowing the first portion 427 to slide in a direction away from the loading mechanism 404. As the first portion 427 slides away from the loading mechanism 404, the pins 440 slide along the elongated apertures 438 is a same direction causing the respective first and second pivot members 430,432 to pivot and the gripping members 442 of the respective first and second pivot members 430,432 to move toward the fastener guide 402 and into the recesses 502 to the closed position (as illustrated in FIGS. 10, 13, 15, and 17).

Figure 16:
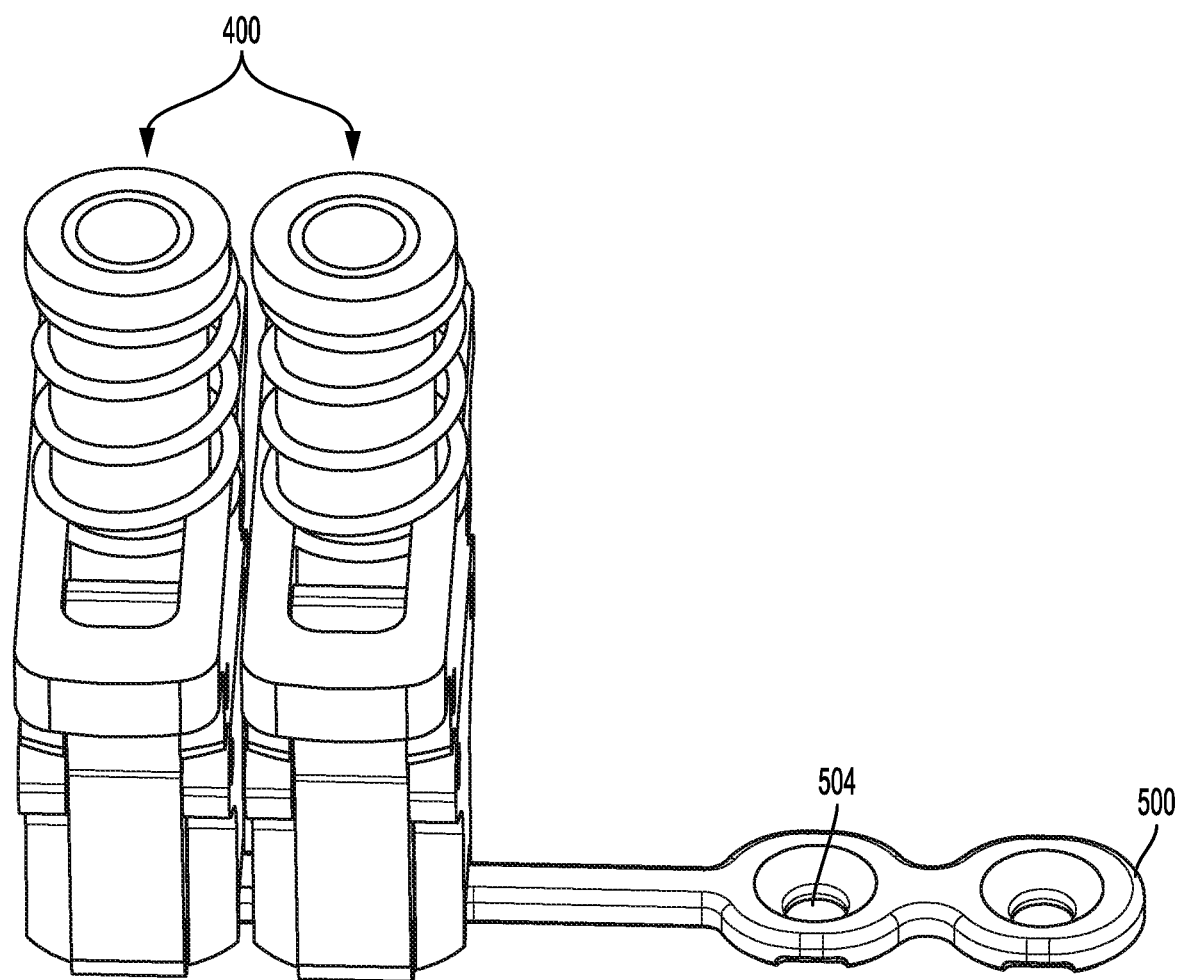
FIG. 16 illustrates a perspective view of the implant positioning device of FIG. 10 coupled to more than one plate according to the disclosure.
Figure 17:
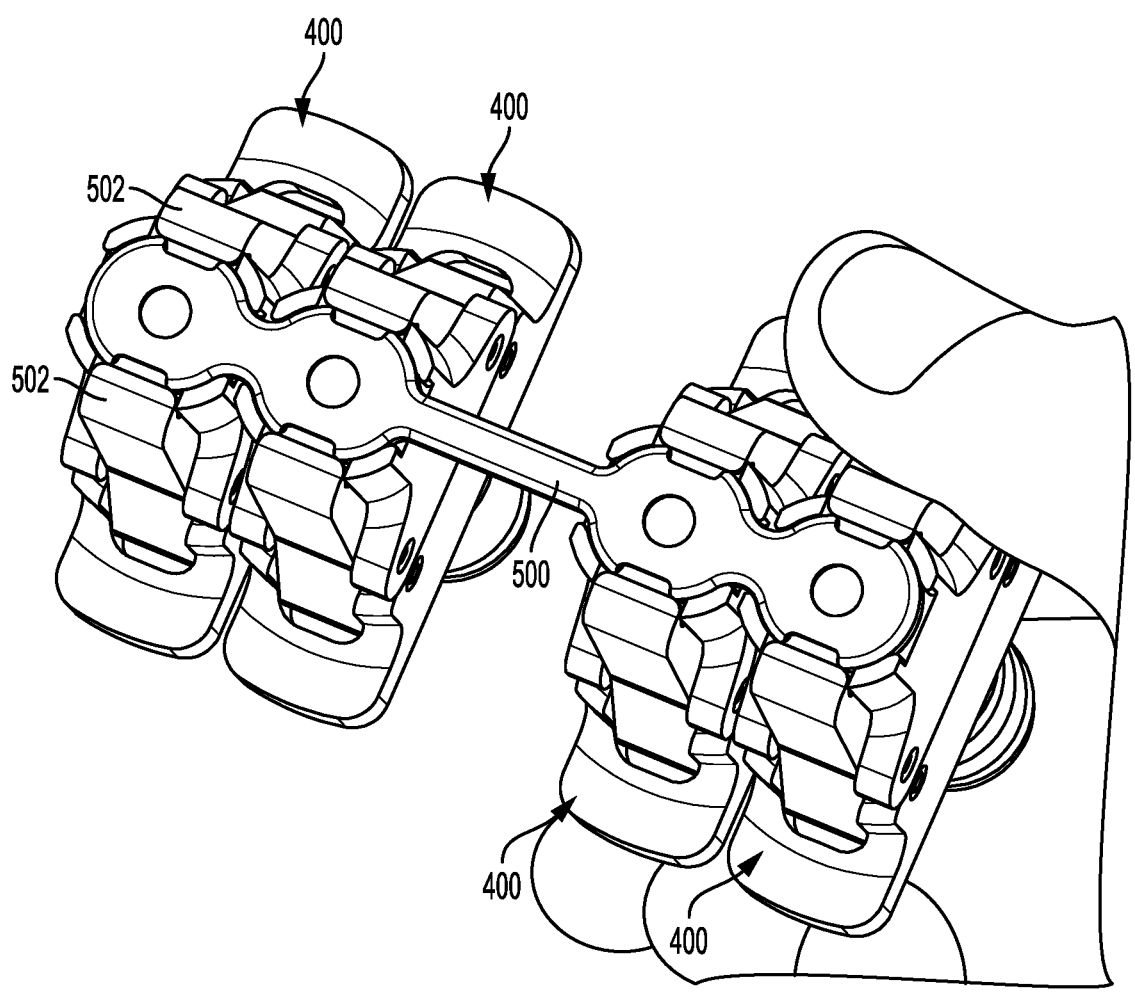
FIG. 17 illustrates a perspective bottom view of the implant positioning device of FIG. 10 coupled to more than one plate according to the disclosure.

Referring to FIG. 16, more than one positioning device 400 may be used with a single fixation device (such as plate 500). For example, respective positioning devices 400 may be coupled to the plate 500 to align fasteners with each respective fastener aperture 504. While plate 500 is used for illustrative purposes, any of the implantable fixation devices disclosed herein may be used in conjunction with the positioning device 400.

The present disclosure also relates to cable locking and anchoring devices and systems. Such devices and systems may be used in a number of surgical procedures, for example, relating to trauma, hips, knees, foot/ankle, spine, craniomaxillofacial, etc., as described in further detail below, to create and/or hold tension on a cable or other wire of the type.

Figure 18:
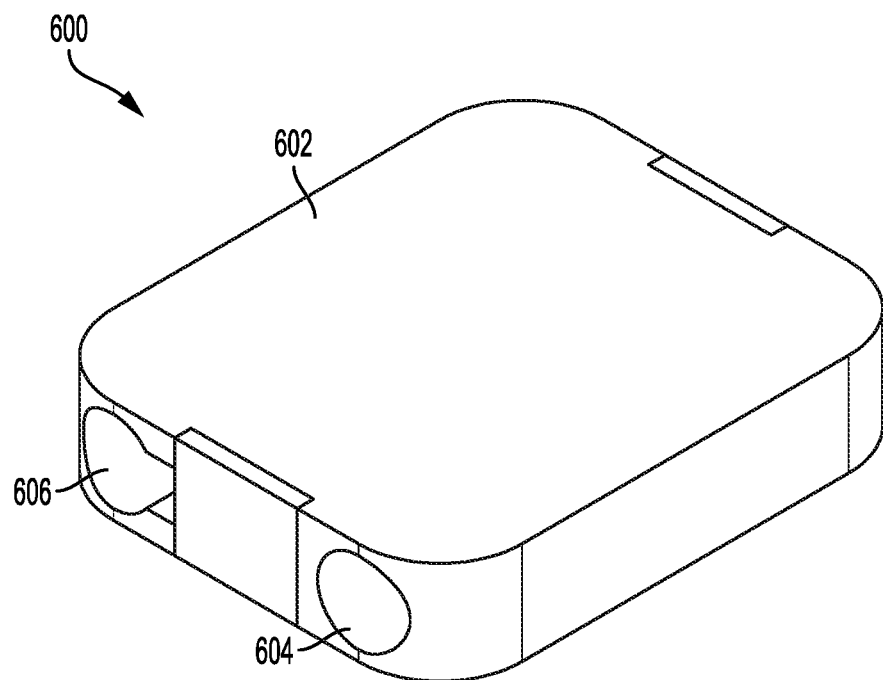
FIG. 18 illustrates a perspective view of a cable locking device according to an embodiment of the disclosure.
Figure 19:
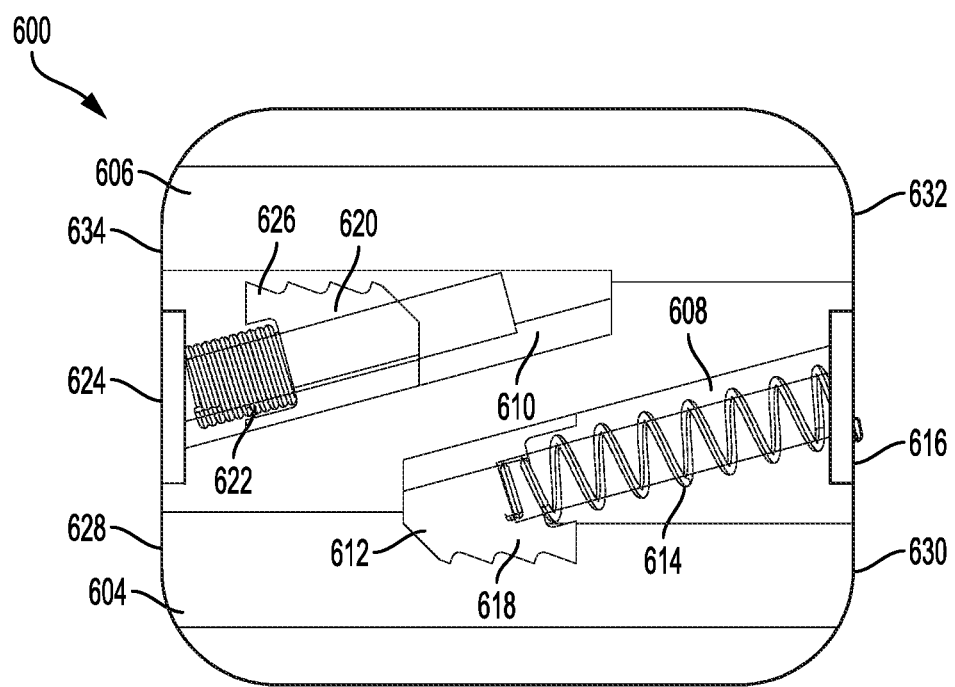
FIG. 19 illustrates an internal view of the cable locking device of FIG. 18 according to the disclosure.

FIGS. 18 and 19 illustrate an locking device 600 according to an embodiment of the disclosure. As illustrated, the device 600 includes a housing 602 that may be a single monolithic housing or include multiple portions coupled together. FIG. 19 illustrates the device 600 in phantom showing internal components of the device 600. The device 600 includes a first bore 604 and a second bore 606 extending through the housing 602. As illustrated the first bore 604 and the second bore 606 are parallel to one another; however, they may be oriented in differing orientations.

The housing 602 also includes a first cutout 608 and a second cutout 610 internal to the housing 602. The first cutout 608 is substantially triangular shaped and is in communication with the first bore 604. A first gripping member or pawl 612 is disposed in the first cutout 608, and a first bias member 614 is disposed between the first pawl 612 and a side 616 of the housing 602. The first bias member 614 biases the first pawl 612 in a direction away from the side 616 and causes teeth 618 of the first pawl 612 to protrude into the first bore 604. As illustrated, the first bias member 614 and first pawl 612 are angularly positioned (for example, an angle of about 15 degrees to about 45 degrees) with respect to the first bore 604.

Similarly, the second cutout 610 is substantially triangular shaped and is in communication with the second bore 606. A second gripping member or pawl 620 is disposed in the second cutout 610, and a second bias member 622 is disposed between the second pawl 620 and a side 624 (opposite side 616) of the housing 602. The second bias member 622 biases the second pawl 620 in a direction away from the side 624 and causes teeth 626 of the second pawl 620 to protrude into the second bore 606. As illustrated, the second bias member 622 and second pawl 620 are angularly positioned (for example, an angle of about 15 degrees to about 45 degrees) with respect to the second bore 606.

The angular displacement of the first bias member 614 and first pawl 612 with respect to the first bore 604, and the second bias member 622 and second pawl 620 with respect to the second bore 606 allow for ends of a cable to be inserted onto the respective first bore 604 and second bore 606 and lock the cable in place (i.e., from being removed from the respective first bore 604 and second bore 606).

For example, an end of a cable may be inserted into an end 628 of the first bore 604 and threaded through the first bore 604 to end 630 of the first bore 604. As the cable moves from the end 628 to the end 630, the cable causes the first pawl 612 to retract into the first cutout 608 and compress the first bias member 614 (such as, the position of the second pawl 620). This allows the cable to pass through the first bore 604. However, the first pawl 612 is being continuously biased back toward the first bore 604 by the first bias member 614 (such as the position of the first pawl 612). Thus, when the cable is pulled or tensioned in a direction from the end 630 to the end 628, the teeth 618 of the first pawl 612 grip the cable and prevent the cable from moving in a direction from the end 630 to the end 628 (i.e., being removed from the first bore 604).

Another end of the cable (or an end of a different cable) may be inserted into an end 632 of the second bore 606 and threaded through the second bore 606 to end 634 of the second bore 606. As the cable moves from the end 632 to the end 634, the cable causes the second pawl 620 to retract into the second cutout 610 and compress the second bias member 622. This allows the cable to pass through the second bore 606. However, the second pawl 620 is being continuously biased back toward the second bore 606 by the second bias member 622 (such as the position of the first pawl 612). Thus, when the cable is pulled or tensioned in a direction from the end 634 to the end 632, the teeth 626 of the second pawl 620 grip the cable and prevent the cable from moving in a direction from the end 634 to the end 632 (i.e., being removed from the second bore 606).

The device 600 may be used in trauma applications or any application in which a cable may be wrapped around a bone or other body part and tensioned. Essentially, one end of the cable may be placed through the first bore 604. The cable may then be wrapped around a bone or other body part to hold separated portions together for healing. The other end of the cable may then be inserted through the second bore 606. The cable may also be tensioned from either end to securely hold the separated portions of the bone or other body part together.

Figure 20:
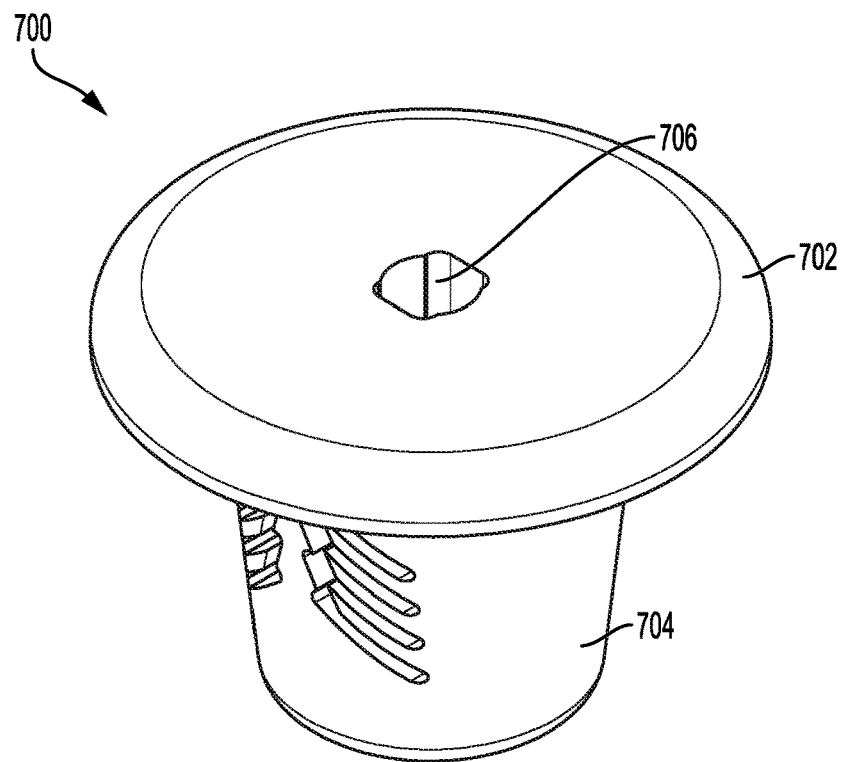
FIG. 20 illustrates a perspective view of another cable locking device according to an embodiment of the disclosure.
Figure 21:
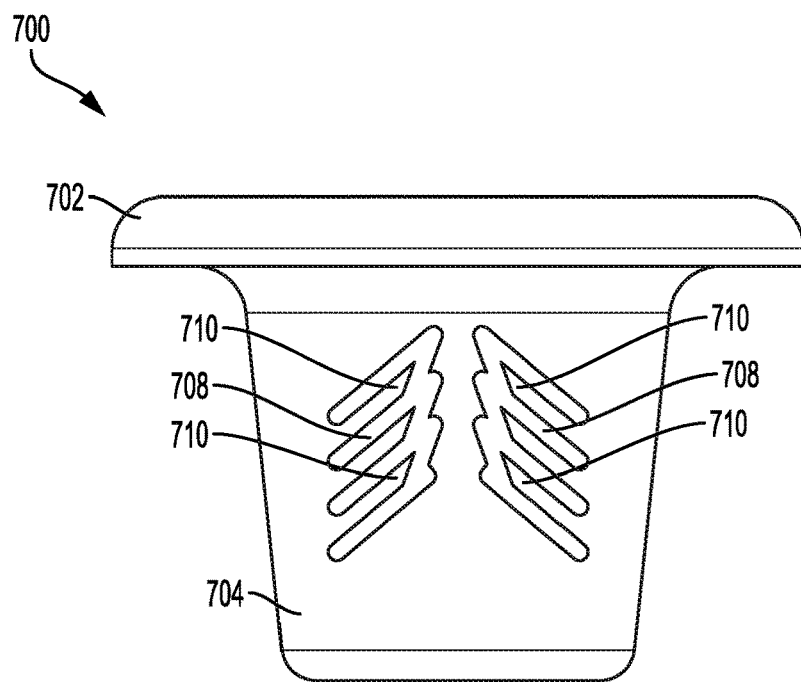
FIGS. 21 and 22 illustrate side view of the cable locking device of FIG. 20 according to the disclosure.
Figure 22:
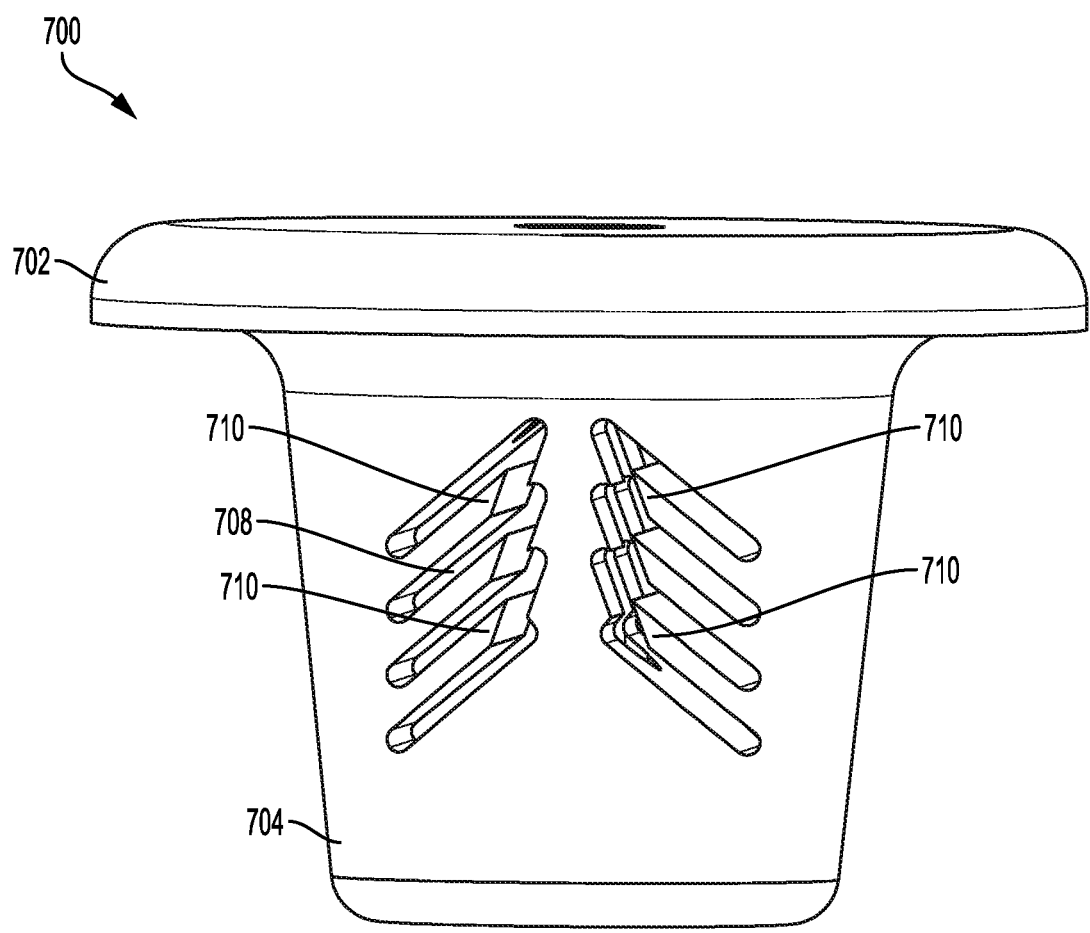

FIGS. 20-22 illustrate another locking device 700 according to an embodiment of the disclosure. As illustrated, the device 700 may be a monolithic single piece, including a flange portion 702 and a body portion 704 extending from the flange portion 702 in a direction substantially perpendicular to a plane of the flange portion 702. A through bore 706 may extend through the flange portion 702 and the body portion 704 for receiving a cable or other wire (which may be any element that may be tensioned). The device 700 also includes one or more slots 708 extending through the body portion 704 forming teeth 710.

As illustrated, the slots 708 and teeth 710 are angularly displaced with respect to the plane of the flange portion 702 to provide teeth 710 extending from the body portion 704 at an angle toward the flange portion 702. This allows a cable to be inserted through the bore 706 from a bottom of the body portion 704 and exiting a top of the flange portion 702. The teeth 710 grip the cable and prevent the cable from being pulled back through the device 700.

In an example, the body portion 704 may be inserted into a bore or counter bore in a bone and the flange portion 702 prevents the device 700 from being pulled through the counter bore. In this respect, a cable may be inserted through the bore 706 from a bottom of the body portion 704 and exiting a top of the flange portion 702. The teeth 710 grip the cable and prevent the cable from being pulled back through the device 700. The cable may be wrapped around a bone or other body part and tensioned. One such procedure the device 700 may be used in is ankle syndesmosis. The device 700 may also be used in other procedures relating to trauma, hips, knees, foot/ankle, spine, craniomaxillofacial, etc.

Figure 23:
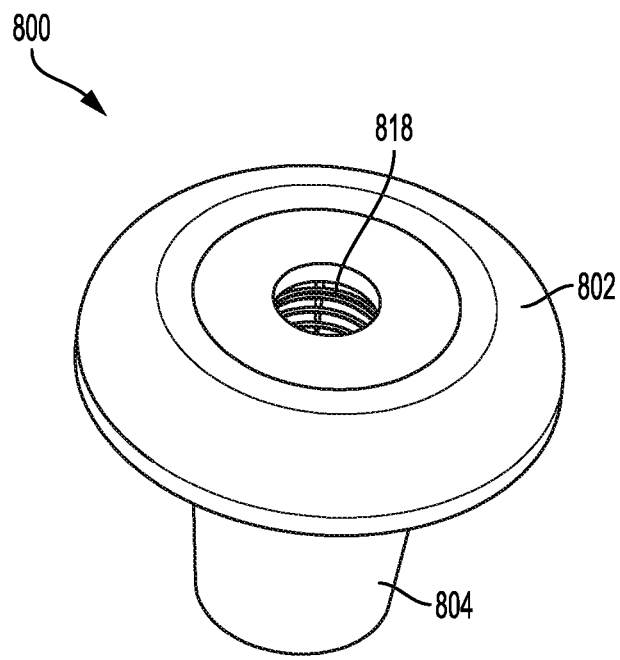
FIG. 23 illustrates a perspective view of another cable locking device according to an embodiment of the disclosure.
Figure 24:
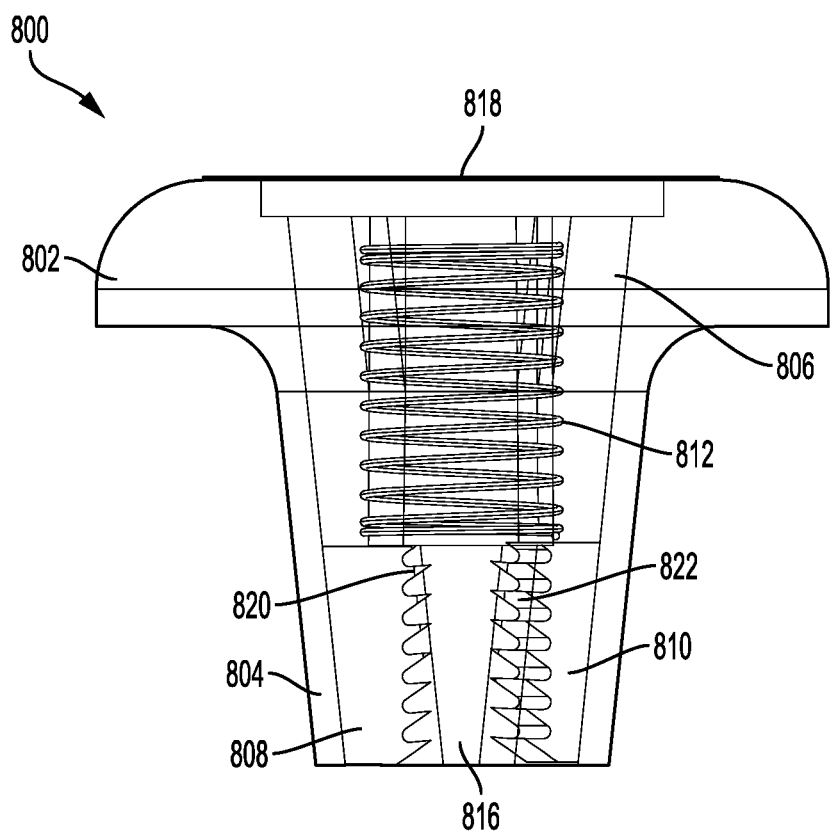
FIG. 24 illustrates an internal view of the cable locking device of FIG. 23 according to the disclosure.

FIGS. 23 and 24 illustrate another locking device 800 according to an embodiment of the disclosure. As illustrated, the device 800 includes a flange portion 802 and a body portion 804 extending from the flange portion 802 in a direction substantially perpendicular to a plane of the flange portion 802. A through bore 806 may extend through the flange portion 802 and the body portion 804 for receiving a cable or other wire (which may be any element that may be tensioned). As illustrated in FIG. 24, the through bore 806 has a larger diameter proximal to the flange portion 802 and decreases in diameter as the through bore 806 extends through the body portion 804.

The device 800 also includes a first pawl 808 and a second pawl 810 disposed in the through bore 806. A bias member 812 is disposed in the through bore 806 proximal to the flange portion 802; and between the first and second pawls 808, 810 and the flange portion 802. The bias member 812 exerts a bias force on the first and second pawls 808, 810 in a direction away from the flange portion 802.

The tapering of the through bore 806, and the bias member 812 and first and second pawls 808, 810 allow for an end of a cable to be inserted into the body portion 804 at aperture 816, through the through bore 806, and exit an aperture 818 in the flange portion 802. The bias member 812 and first and second pawls 808, 810 lock the cable in place (i.e., from being removed from the device 800).

For example, an end of a cable may be inserted into aperture 816 and pushed or threaded through the through bore 806 an out of the aperture 818 in the flange portion 802. As the cable moves though the through bore 806, the cable causes the first and second pawls 808, 810 to move against the bias force of the bias member 812 toward the flange portion 802. This allows the cable to pass through the through bore 806. However, the first and second pawls 808, 810 are being continuously biased away from the flange portion 802 by the bias member 812. Thus, when the cable is pulled or tensioned in a direction from the flange portion 802 to the body portion 804, the teeth 820 of the first pawl 808 and teeth 822 of the second pawl 810 grip the cable and prevent the cable from being removed from the device 800. The cable may be wrapped around a bone or other body part and tensioned. One such procedure the device 800 may be used in is ankle syndesmosis. The device 800 may also be used in other procedures relating to trauma, hips, knees, foot/ankle, spine, craniomaxillofacial, etc.

As illustrated in FIG. 24, the cable (not illustrated) would pass through the bias member 812 when inserted into the device 800. In an aspect, the device 800 may include a sleeve (not shown) that provides separation or blocks the cable from contacting the bias member 812. Other mechanisms may also be used to prevent the cable from contacting the bias member 812 as well.

Figure 25:
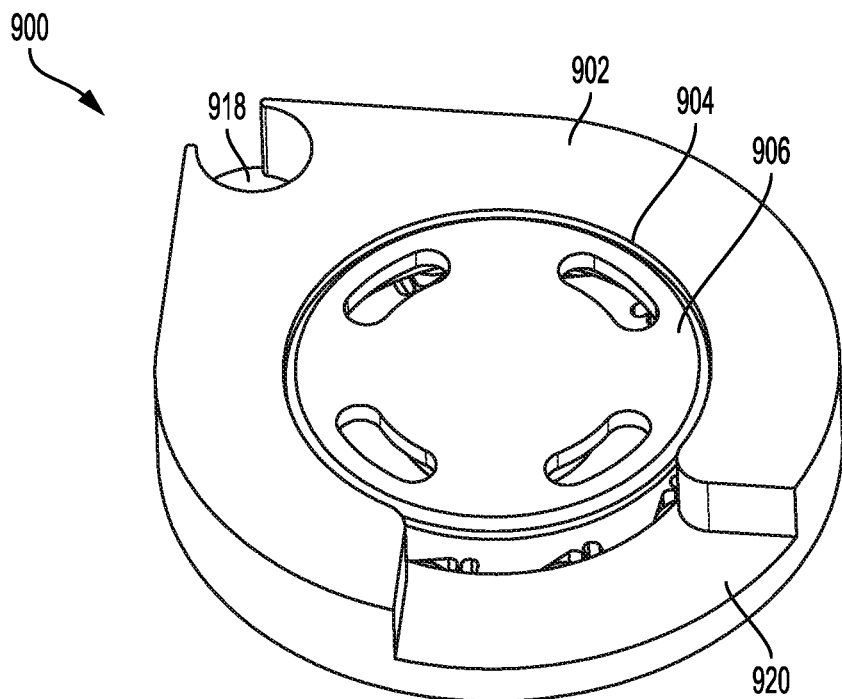
FIG. 25 illustrates a perspective view of a roller clutch implantable device according to an embodiment of the disclosure.
Figure 26:
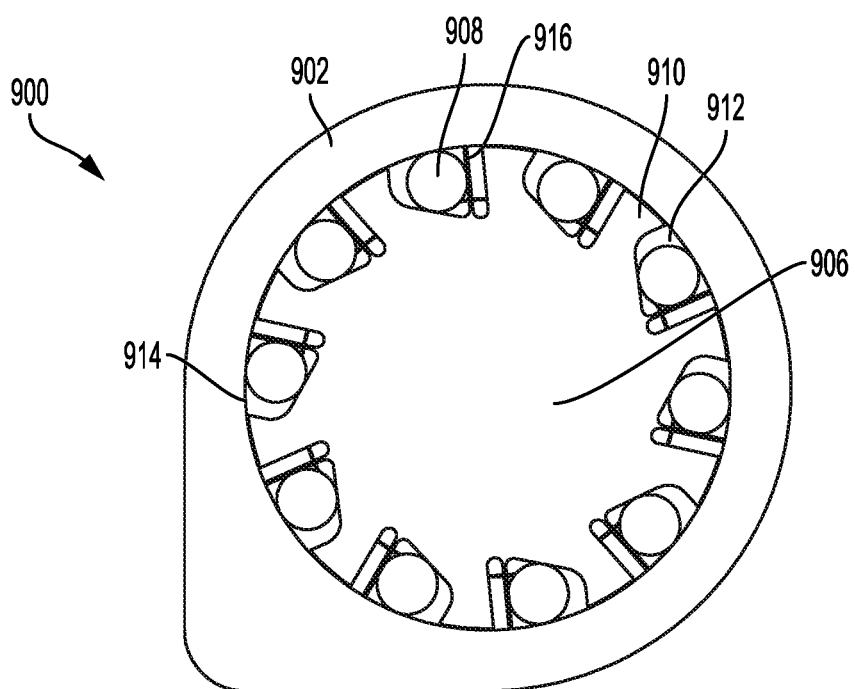
FIG. 26 illustrates an internal view of the roller clutch implantable device of FIG. 25 according to the disclosure.

In other embodiments, the present disclosure relates to roller clutch and ratchet mechanisms that may be used to add tension to cables. FIGS. 25 and 26 illustrate a roller clutch device 900 according to an embodiment of the disclosure. As illustrated, the device 900 includes a base 902 having a recess or well 904, and a wheel 906 and bearings/rollers 908 disposed in the recess 904.

The wheel 906 includes a number of protrusions 910 and cutouts 912 that receive the rollers 908. The cutouts 912 are ramp shaped to allow the wheel 906 to rotate freely in a first direction, such as a counter clockwise direction as illustrated in FIG. 26. The ramped features of the cutouts 912 also prevent the wheel 906 from being rotated in the reverse direction, such as a clockwise direction as illustrated in FIG. 26. The wheel 906 is prevented from being rotated in the reverse direction (such as a clockwise direction as illustrated in FIG. 26) by the rollers 908. As the wheel 906 is rotated in the reverse direction, the ramped features of the cutouts 912 cause the rollers 908 to contact and exert a force on an inner wall 914 of the recess 904 thereby preventing the wheel 906 from rotating. To minimize an amount of travel of the wheel 906 when rotated in the reverse direction, the wheel may include bias members 916 (such as springs or leaf springs) that bias the rollers 908 to a position that is in contact with the inner wall 914.

As illustrated in FIG. 25, the base 902 may also include a capture recess 918 for receiving an end of a cable or other tensioning element, and a recessed opening 920 that allows an opposite end of the cable to be inserted into the wheel 906 and tensioned. Thus, the device 900 may be used in any surgical procedure where a cable or other tensioning element is wrapped around a bone (separated or otherwise) or other body part and tensioned (by rotating the wheel 906 causing the cable to be wound around the wheel 906).

Figure 27:
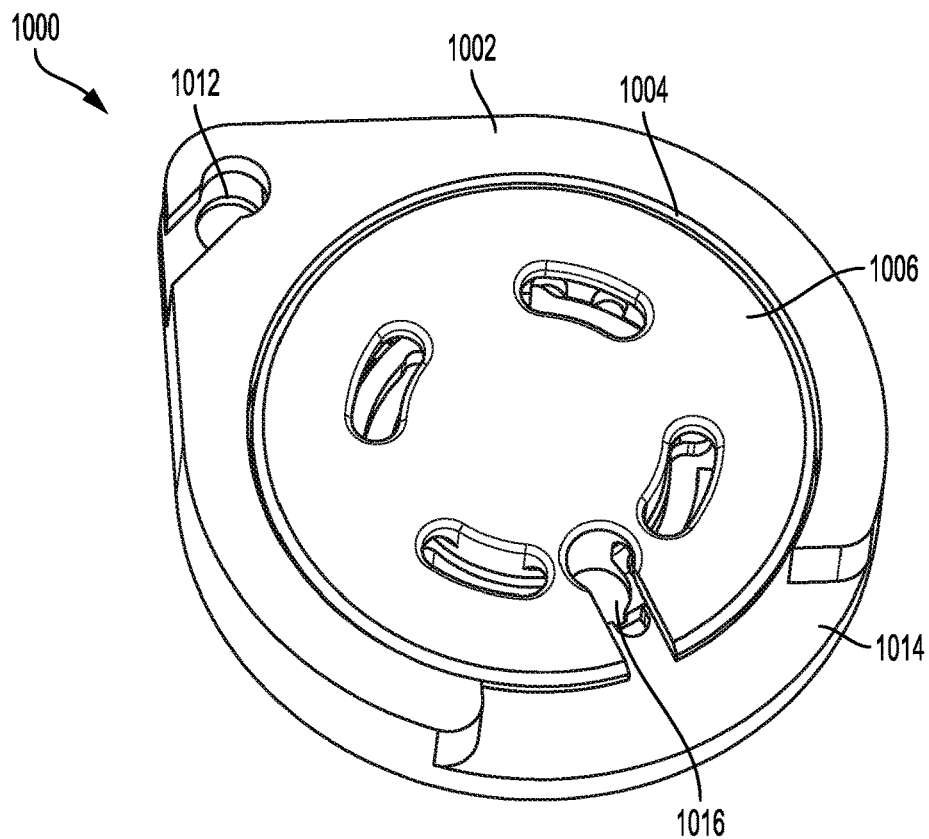
FIG. 27 illustrates a perspective view of a ratcheting implantable device according to an embodiment of the disclosure.
Figure 28:
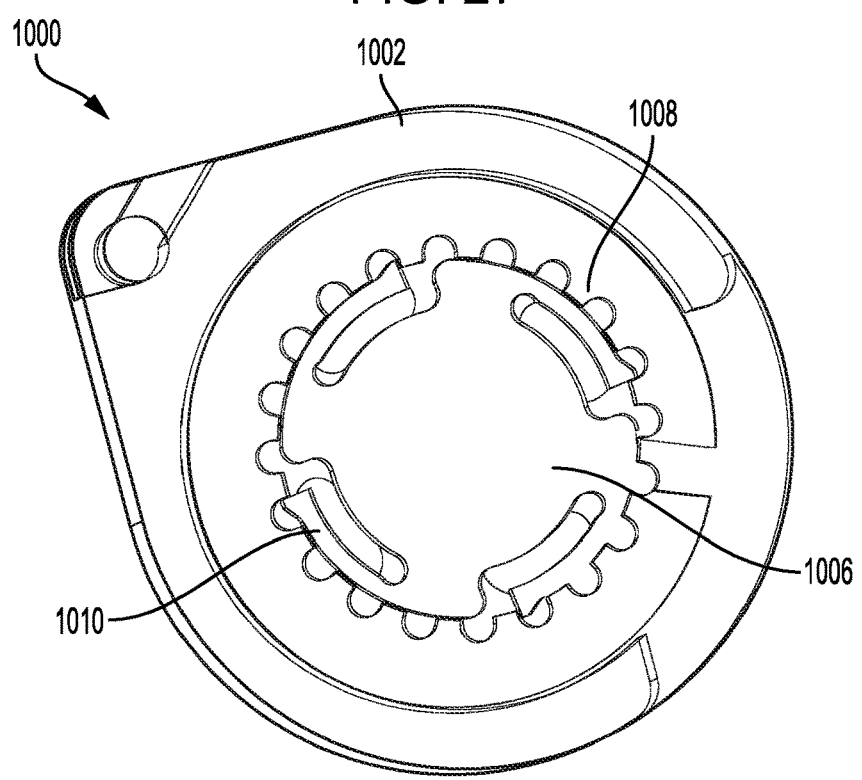
FIG. 28 illustrates an internal view of the ratcheting implantable device of FIG. 27 according to the disclosure.

FIGS. 27 and 28 illustrate a ratcheting device 1000 according to an embodiment of the disclosure. As illustrated, the device 1000 includes a base 1002 having a ratchet recess or well 1004, and a ratchet wheel 1006. The ratchet recess 1004 includes a plurality of teeth 1008 around an inner circumference of the ratchet recess 1004 that extend radially inward towards a center of the ratchet recess 1004.

The ratchet wheel 1006 is disposed in the ratchet recess 1004. The ratchet wheel 1006 includes one or more pawls 1010 configured to engage the teeth 1008 and allow the ratchet wheel 1006 to rotate in one direction while preventing rotation in the opposite direction. As illustrated, the ratchet wheel 1006 includes four pawls 1010 and the ratchet recess 1004 includes twenty teeth 1008. This provides for a ratchet mechanism that locks, thereby preventing rotation in the opposite direction, at about each eighteen degree increment of rotation. However, it should be appreciated that the number of pawls 1010 and teeth 1008 may be increased or decreased to provide a ratchet mechanism that locks, thereby preventing rotation in the opposite direction, at any desired degree increment of rotation.

As illustrated in FIG. 27, the base 1002 may also include a capture recess 1012 for receiving an end of a cable or other tensioning element, and a recessed opening 1014 that allows an opposite end of the cable to be inserted into the ratchet wheel 1006 and tensioned. In an aspect, the ratchet wheel 1006 may also include a capture recess 1016 for receiving the opposite end of a cable or other tensioning element. Thus, the device 1000 may be used in any surgical procedure where a cable or other tensioning element is wrapped around a bone (separated or otherwise) or other body part and tensioned (by rotating the wheel 1006 causing the cable to be wound around the wheel 1006).

Figure 29:
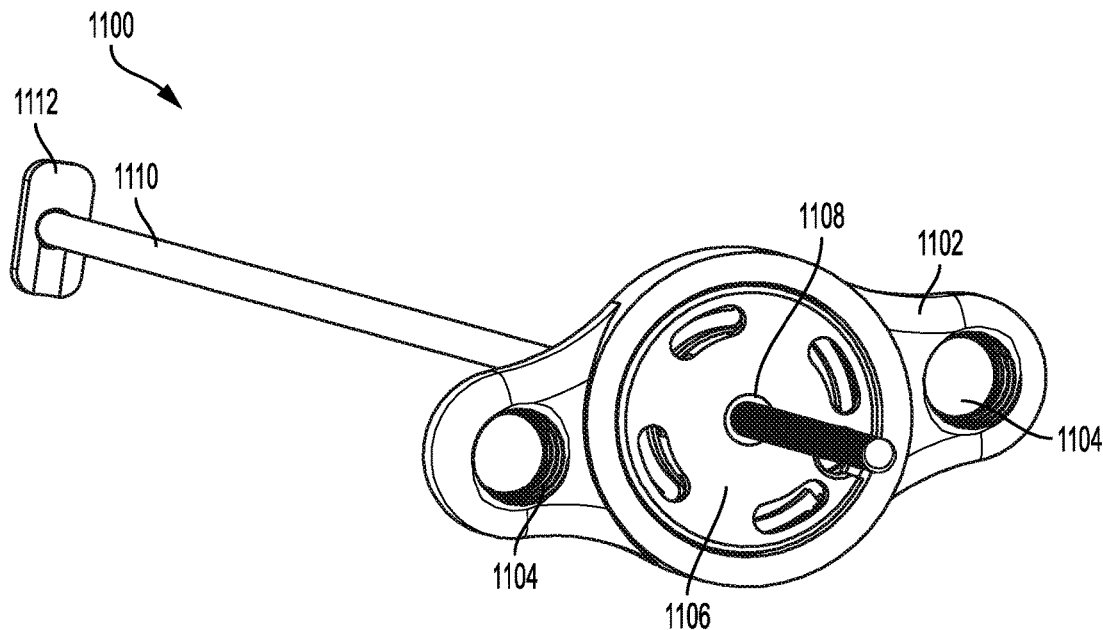
FIG. 29 illustrates a perspective view of another ratcheting implantable device according to an embodiment of the disclosure.
Figure 30:
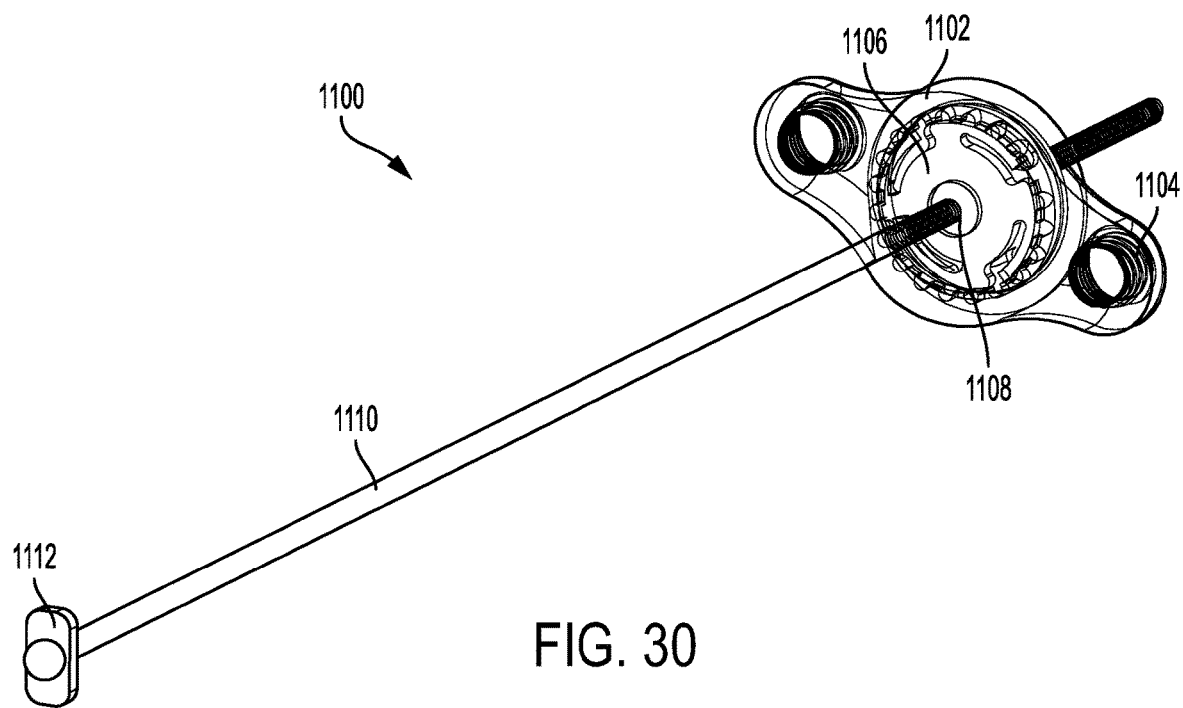
FIG. 30 illustrates an internal view of the ratcheting implantable device of FIG. 29 according to the disclosure.

FIGS. 29 and 30 illustrate another ratcheting device 1100 according to an embodiment of the disclosure. The device 1100 is similar to that of device 1000 described above. For example, the device 1100 includes a similar ratchet mechanism as that of device 1000, but has the differences described below. However, the device 1100 may include a similar roller clutch as that of device 900 instead.

As illustrated, the device 1100 includes a base 1102 and a similar ratchet mechanism as that of device 1000. The base 1102 may also include one or more fastener apertures 1104 for receiving fasteners that fasten the base 1102 to a bone or other body part. In this embodiment, the wheel 1106 also includes a threaded aperture 1108 that receives a corresponding threaded cable or other locking element 1110.

In an example, the device 1100 may be fastened to a bone or other body part using fasteners. A through bore may be created in the bone that receives the locking element 1110 and aligns with the threaded aperture 1108. The locking element 1110 may be inserted through the through bore and into the threaded aperture 1108. The wheel 1106 may then be rotated to thread the locking element 1110 through the bone to being a flange portion 1112 into contact with the bone. The wheel 1106 may be rotated to tension the locking element 1110 while the flange portion 1112 prevents the locking element 1110 from being pulled though the bone. The ratcheting mechanism or roller clutch mechanism of the wheel prevents the wheel from rotating in the reverse direction and loosening the locking element. One such procedure the device 1100 may be used in is ankle syndesmosis. The device 1100 may also be used in other procedures relating to trauma, hips, knees, foot/ankle, spine, craniomaxillofacial, etc.

Figure 31:
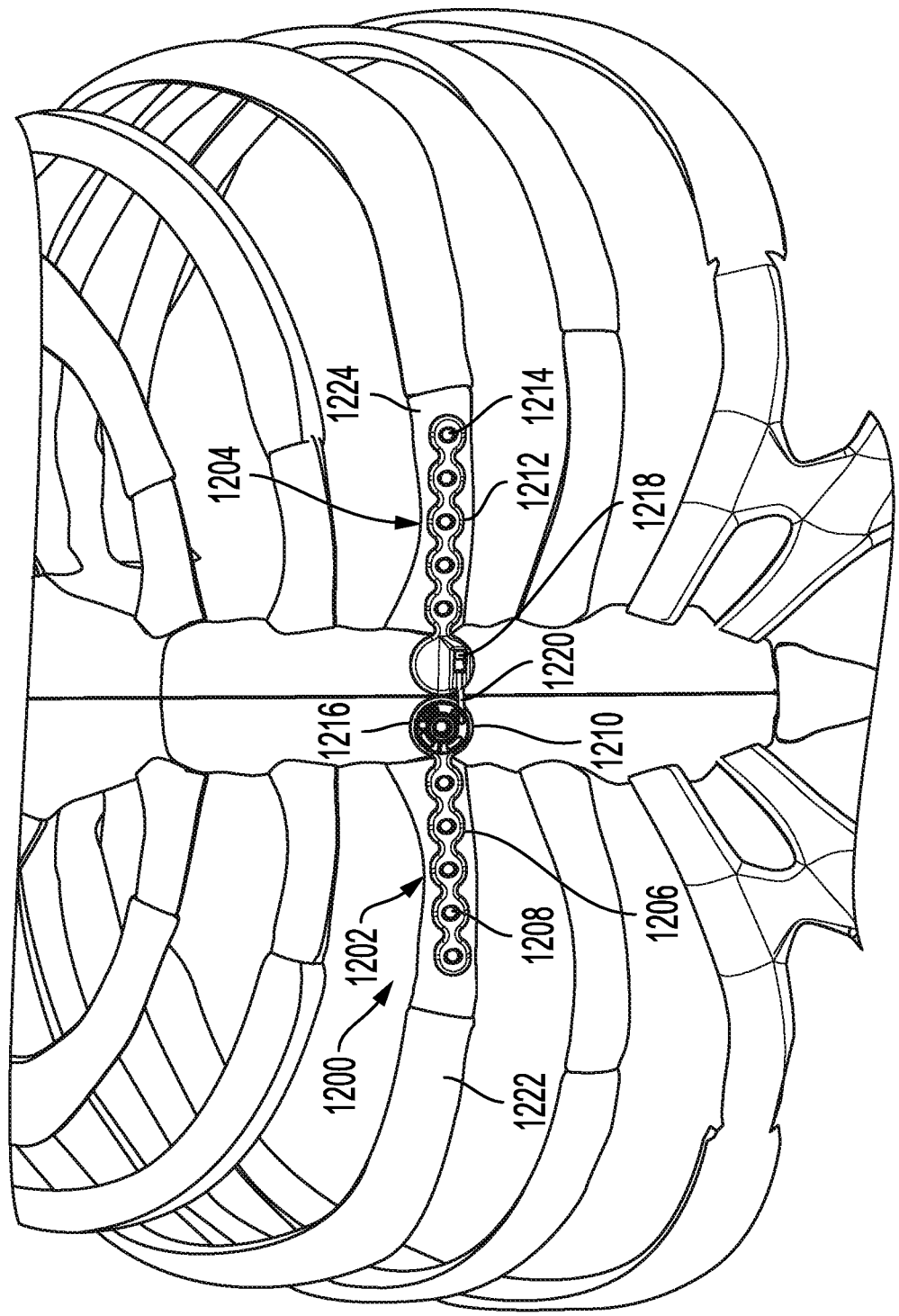
FIG. 31 illustrates a perspective view of an implantable fixation device coupled to one or more ribs of a patient according to an embodiment of the disclosure.

In still other embodiments, the present disclosure relates to implantable fixation devices for use in sternal closure; however, the device may be used for other procedures in which separated bone portions or other body parts are brought together for healing. FIG. 31 illustrates an implantable fixation device 1200 according to an embodiment of the disclosure. As illustrated, the device 1200 includes a first plate 1202 and a second plate 1204.

The first plate 1202 includes a longitudinal portion 1206 having one or more fastener apertures 1208. The first plate 1202 also includes a ratchet mechanism 1210, which may be a similar ratchet mechanism as that described above with respect to the device 1000. The ratchet mechanism 1210 may also be a roller clutch mechanism similar to that described above with respect to the device 900 instead.

The second plate 1204 also includes a longitudinal portion 1212 having one or more fastener apertures 1214. As illustrated, the ratchet mechanism 1210 and the second plate 1204 each include capture recesses 1216 and 1218, respectively, for receiving ends of a locking element 1220.

As illustrate in FIG. 31, the device 1200 may be used for bringing together two portions of a separated sternum. In this respect, the first and second plates 1202, 1204 may be fastened to ribs 1222 and 1224, respectively, by inserting fasteners into the ribs 1222 and 1224 through fastener apertures 1208, 1214, respectively. The two separated portions of the sternum may then be brought together and the ends of the locking element 1220 inserted into the corresponding capture recesses 1216 and 1218. The ratchet mechanism 1210 may then be used to urge the separated portions of the sternum together. It should be appreciated that the device 1200 may be installed on the ribs either prior to or after separation of the sternum. Further, the locking element 1220 allows for the locking element to be cut to allow for reentry into the chest cavity, and then replaced to assist in urging the separated portions of the sternum back together. In an aspect, one or more shear pins may also be used in conjunction with the device 1200.

Figure 32:
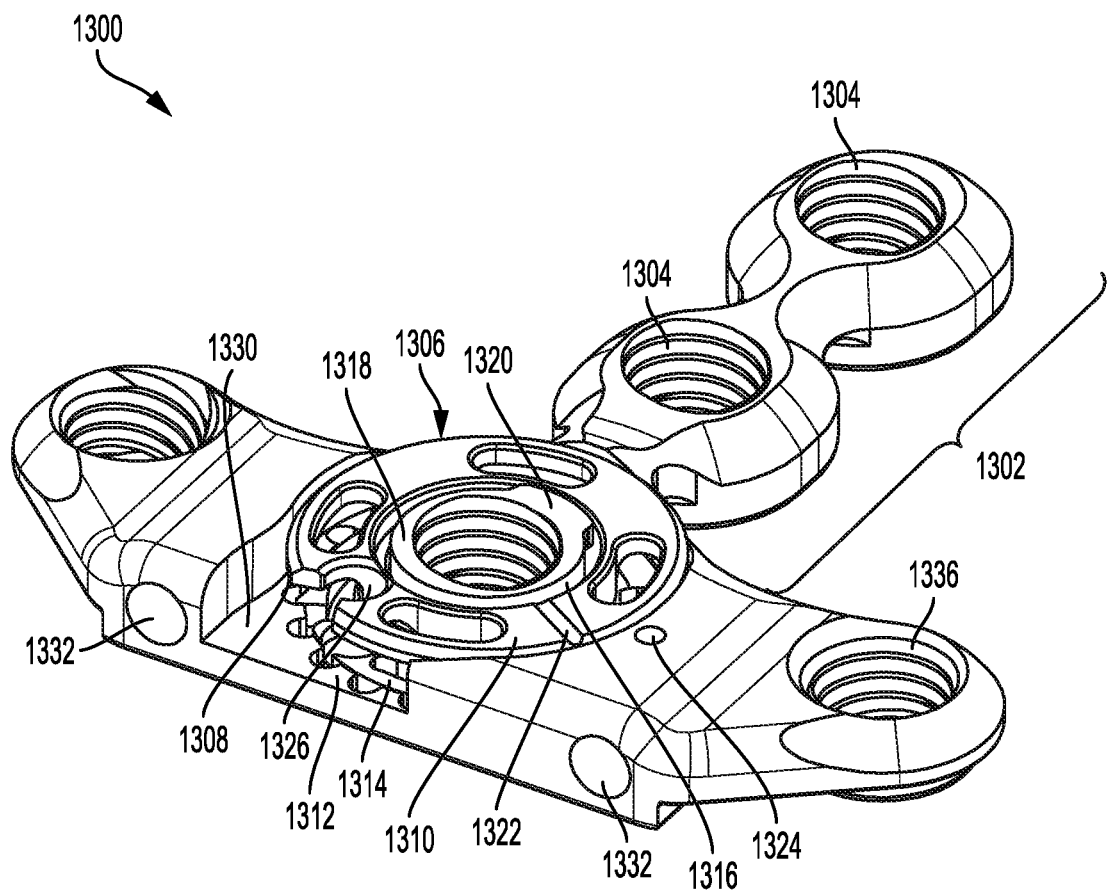
FIG. 32 illustrates a perspective view of another implantable fixation device configured to couple to a rib of a patient according to an embodiment of the disclosure.

FIG. 32 illustrates another implantable fixation device 1300 according to an embodiment of the disclosure. The device 1300 may be similar to the plate 102 disclosed in U.S. Patent Application Publication No. 2015/0119887, entitled Orthopedic Fixation Device, System and Method, filed Oct. 27, 2014, the disclosure of which is incorporated by reference herein in its entirety. The device 1300 may also be used in conjunction with the plate 104 disclosed in U.S. Patent Application Publication No. 2015/0119887 and illustrated in FIG. 33 of the present disclosure.

The device 1300 differs from the device 102 disclosed in U.S. Patent Application Publication No. 2015/0119887 in that the device 1300 includes an additional portion 1302 extending from the plate that includes one or more fastener apertures 1304. This additional portion 1302 may extend onto a rib to provide for additional support. The portion 1302 may extend from a center of the plate (as illustrated in FIG. 32) or may extend from other locations along the edge of the plate.

In general, the device 1300 includes a ratchet mechanism 1306. The ratchet mechanism 1306 includes a ratchet recess or well 1308 and a ratchet wheel 1310. The ratchet recess 1308 is located in substantially a central portion of a top portion (i.e., facing away from a body/bone onto which the plate may be attached) of the device 1300. As illustrated in FIG. 32, the ratchet recess 1308 includes a plurality of teeth 1312 around a circumference of the ratchet recess 1308 that extend radially inward towards a center of the ratchet recess 1308.

The ratchet wheel 1310 is removably disposed in the ratchet recess 1308. The ratchet wheel 1310 includes one or more pawls 1314 configured to engage the teeth 1312 and allow the ratchet wheel 1310 to rotate in one direction while preventing rotation in the opposite direction. The ratchet wheel 1310 also includes an aperture 1316 including a ledge extending substantially circumferentially around the aperture and extending radially inward toward a center of the aperture 1316. The ratchet wheel attachment utilizes a cut-out or groove area configured to receive a protrusion of a boss 1318. The boss 1318 extends in an upward direction from a central portion of the ratchet recess 1308 and includes the protrusion 1320 proximal to a top edge of the boss 1318 that extends radially outward from a center of the boss 1318. This protrusion and groove arrangement allows for the wheel 1310 to be put into place and then held in the well. Once the wheel is advanced, then the protrusion is captured, holding the ratchet wheel 1310 in the wheel well, yet readily removable from the ratchet recess 1308 if necessary by later realigning the protrusion and groove.

To facilitate ease of assembly and disassembly, the ratchet wheel 1310 may include an indicator 1322 and the device 1300 may include a corresponding indicator 1324, that when aligned indicate that the cut-out is aligned with the protrusion 1320. This allows a user to visually identify the correct position of the ratchet wheel 1310 to install or remove the ratchet wheel 1310.

The ratchet wheel 1310 also includes a locking element capture receptacle 1326 and an annular channel. The locking element capture receptacle 1326 is configured to receive an end of a locking element 1328 (illustrated in FIG. 33). The channel is configured to receive and allow the locking element 1328 (illustrated in FIG. 33) to be coiled around the ratchet wheel 1310 to tighten the locking element 1328 (illustrated in FIG. 33). The ratchet wheel 1310 may also include one or more tool engaging features, illustrated as oblong apertures. The tool engaging features are configured to receive a corresponding male feature of a tool for use in rotating the ratchet wheel 1310 to coil the locking element 1328 (illustrated in FIG. 33) around the ratchet wheel 1310.

The device 1300 includes a cut-out or area of reduced wall height 1330 proximal to the face. This allows the locking element 1328 (illustrated in FIG. 33) to extend from the device 1300 and be coupled to the second device 1400 (illustrated in FIG. 34), as described in further detail hereinafter.

The device 1300 may include one or more shear pin receiving receptacles 1332 in the face. The receiving receptacles 1332 are configured to receive corresponding shear pins 1334 (illustrated in FIG. 33) extending from the second device 1400. This assists in aligning the device 1300 and the device 1400 when installed and used.

The device 1300 may also include one or more threaded fastener apertures 1336 configured to receive corresponding fasteners to couple the device 1300 to a bone or other body part. As illustrated in FIG. 32, the threaded fastener apertures include a first aperture positioned proximal to the first end, a second aperture positioned proximal to the second end, and a third aperture in the boss 1318.

Figure 33:
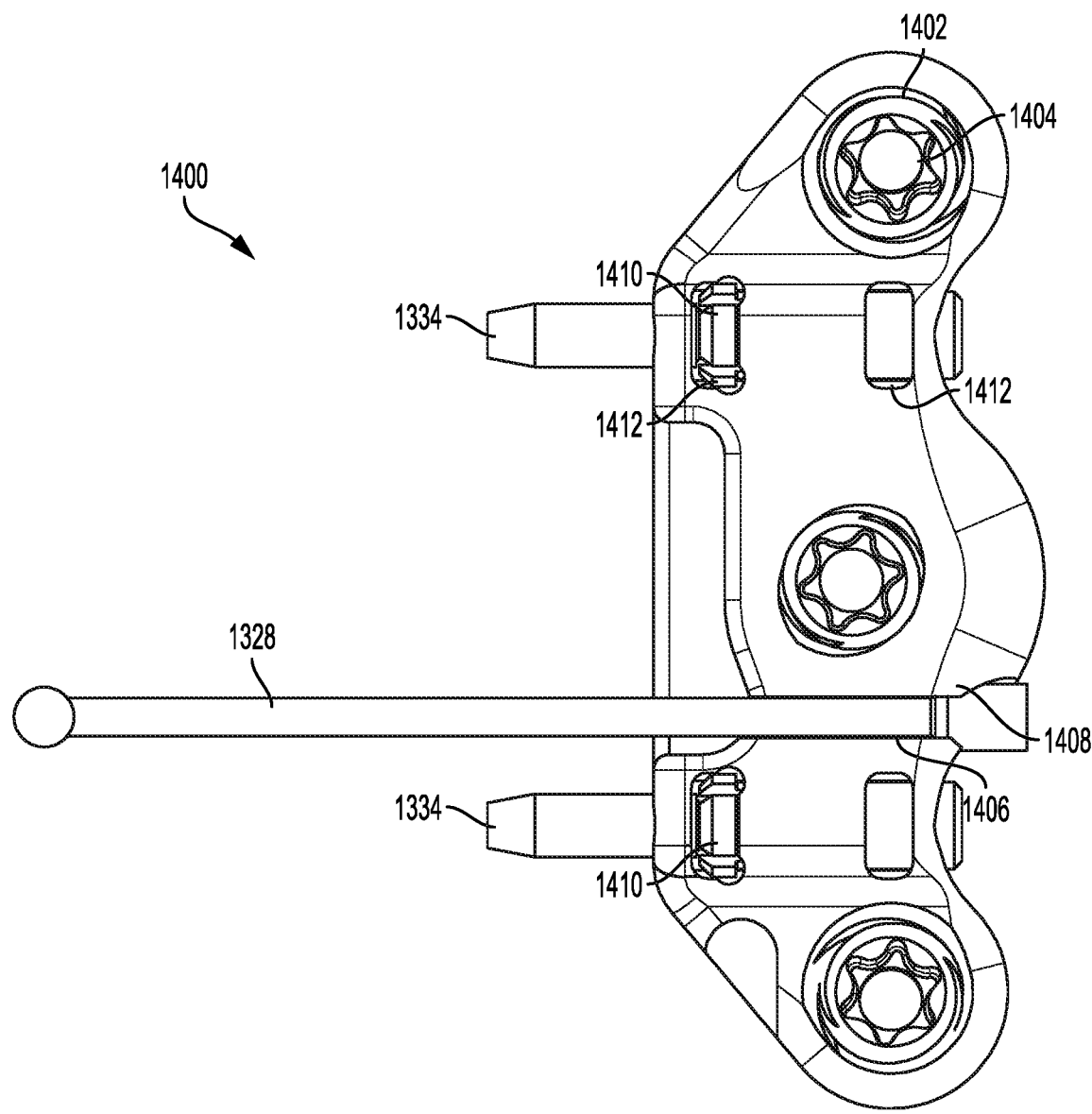
FIG. 33 illustrates a perspective view of another implantable fixation device configured to be used in conjunction with the implantable fixation device of FIG. 32 according to an embodiment of the disclosure.

Referring to FIG. 33, the second device 1400 includes a first end, a second end, and a second face configured to be positioned facing the first face of the device 1300 (illustrated in FIG. 32) in an opposed relationship. Similar to the device 1300, the second device 1400 may include one or more threaded fastener apertures 1402 configured to receive corresponding fasteners 1404 to couple the second device 1400 to a bone or other body part. As illustrated, the threaded fastener apertures include a first aperture positioned proximal to the first end, a second aperture positioned proximal to the second end, and a third aperture substantially in a center of the second device 1400.

The second device 1400 may also include a locking element capture channel 1406 formed in a top of the second device 1400 and extending across the second device 1400 in a substantially perpendicular direction to a longitudinal axis of the second device 1400. The locking element capture channel 1406 is configured to receive an end of the locking element 1328. The locking element capture channel 1406 may also include a stop or ledge 1408 configured to prevent the locking element 1328 from being pulled out of the channel in a direction of the face.

One or more apertures extend through the second device 1400 in a substantially perpendicular direction to the longitudinal axis of the second device 1400. The apertures are configured to receive corresponding shear pins 1334. One aperture may be positioned between the first aperture and the third aperture, and located to align with one of the receiving receptacles 1332 of the device 1300 (illustrated in FIG. 32). Another aperture may be positioned between the second aperture and the third aperture, and located to align with the other of the receiving receptacles 1332 of the device 1300 (illustrated in FIG. 32).

The shear pins 1334 may include deflectable prongs 1410 and the second device 1400 may include corresponding prong receiving receptacles 1412 configured to receive the prongs 1410 to hold the shear pins 1334 in the second device 1400. The prong receiving receptacles provide for a first position of the shear pins 1334, in which ends of the shear pins 1334 are positioned within the apertures and do not extend past the face of the second device 1400. The prong receiving receptacles also provide for a second position of the shear pins 1334, in which ends of the shear pins 1334 extend past the face of the second device 1400, and extend into the receiving receptacles 1332 of the device 1300 (illustrated in FIG. 32) when installed and used to hold two corresponding bone portions together. When the locking element 1328 is installed and the ratchet wheel 1310 is rotated, the locking element 1328 is coiled around the ratchet wheel 1310 to urge the device 1300 and second device 1400 together and into alignment with one another.

Figure 34:
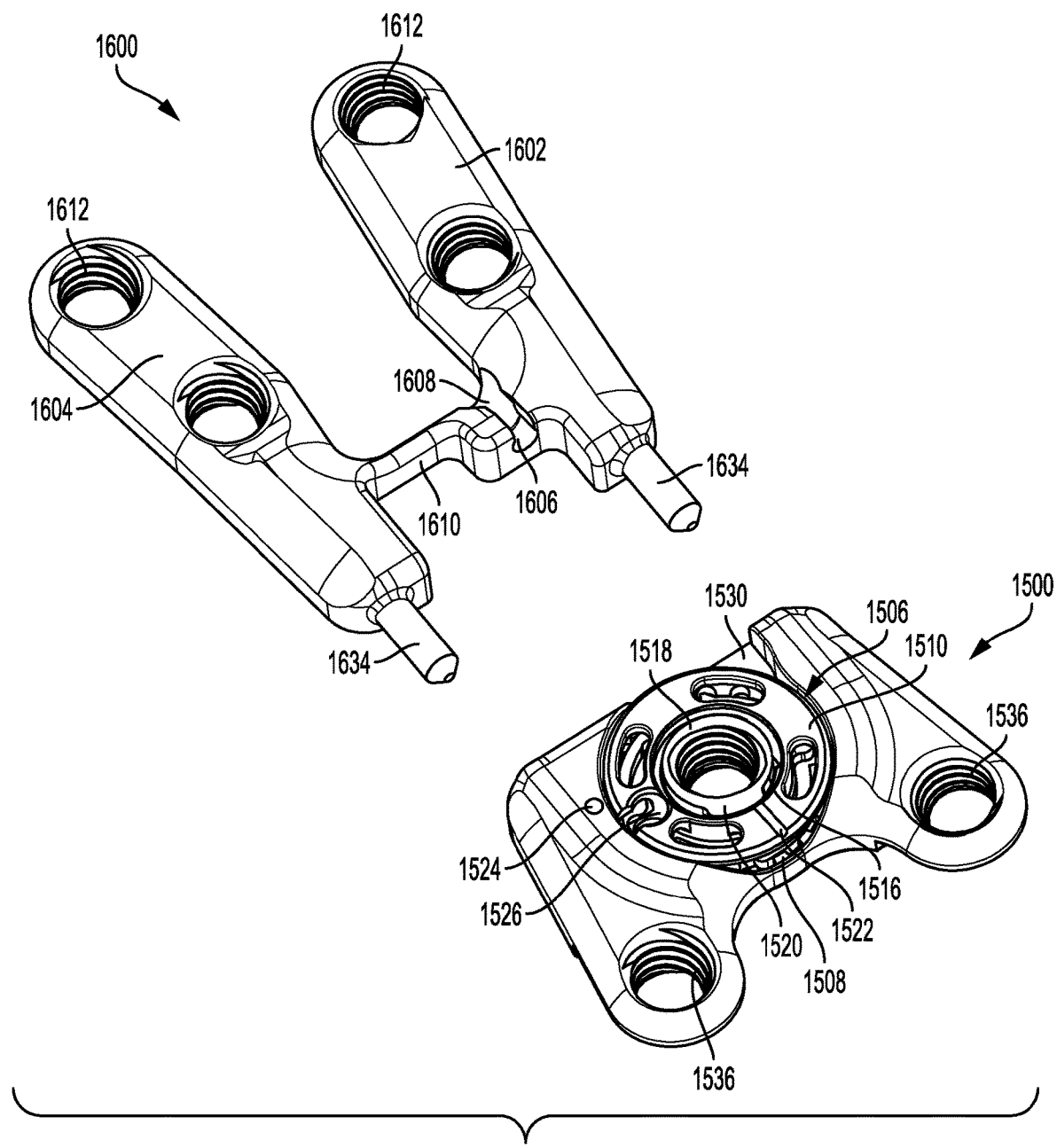
FIG. 34 illustrates a perspective view of a system including implantable fixation devices according to an embodiment of the disclosure.
Figure 35:
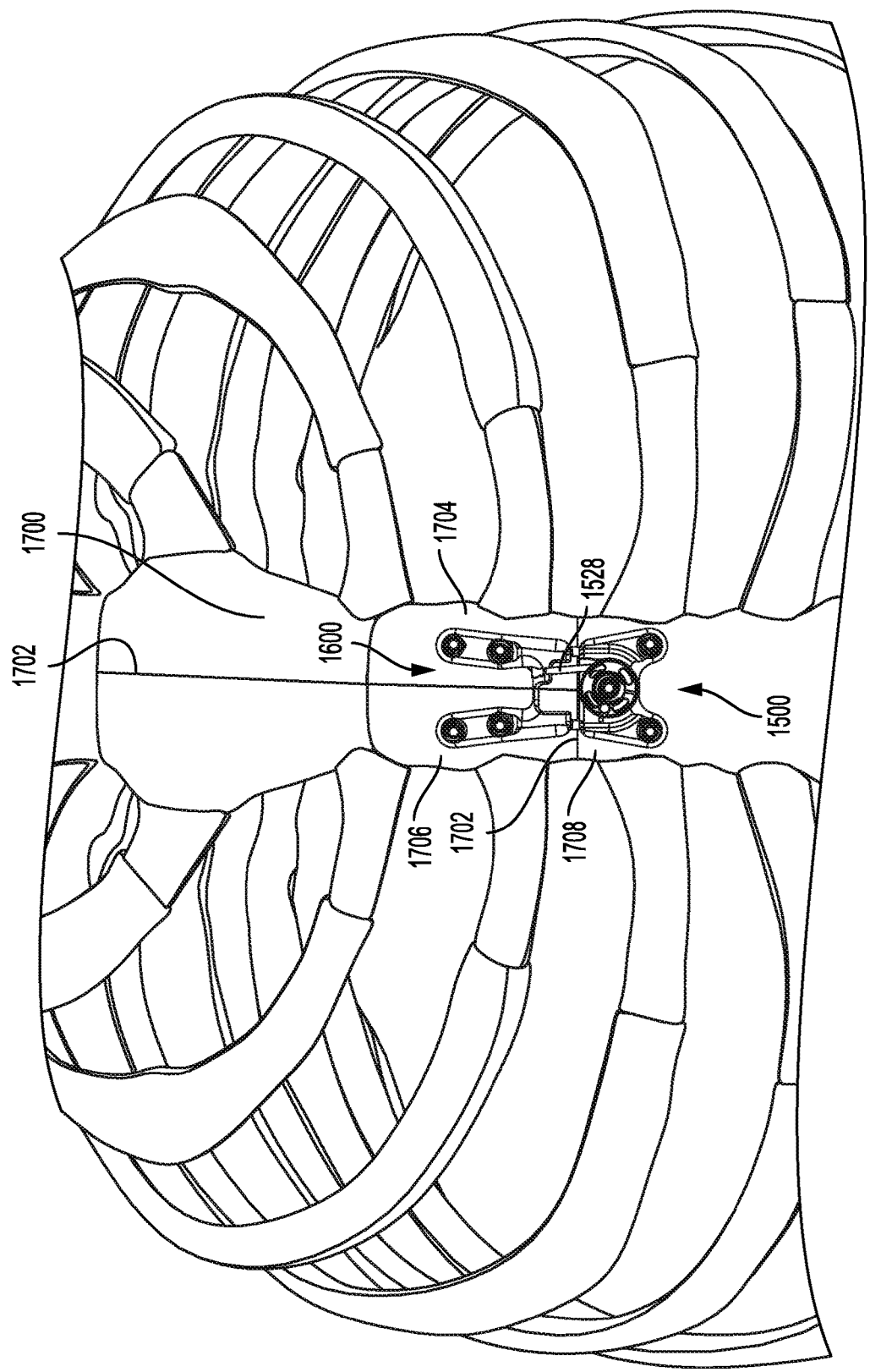
FIG. 35 illustrates a perspective view of the system of FIG. 34 coupled to a sternum of a patient according to the disclosure.

FIGS. 34 and 35 illustrates another implantable fixation device system according to an embodiment of the disclosure. The system includes a first implantable fixation device 1500 and a second implantable fixation device 1600. The first device 1500 is similar to that of the device 1300 described above, but having a different geometry as illustrated in FIG. 34. The device 1500 also cooperates with the device 1600 similar to the way the devices 1300 and 1400 described above cooperate with one another.

In one example, the geometry (including the size and shape) of the devices 1500 and 1600 allow for their use in assisting with closing a sternum that is separated using a "T" incision, such as the incision 1702 illustrated in sternum 1700 of FIG. 35.

The device 1500 includes a plate having a ratchet mechanism 1506. The ratchet mechanism 1506 includes a ratchet recess or well 1508 and a ratchet wheel 1510. The ratchet recess 1508 is located in substantially a central portion of a top portion (i.e., facing away from a body/bone onto which the plate may be attached) of the device 1500. The ratchet recess 1508 includes a plurality of teeth around a circumference of the ratchet recess 1508 that extend radially inward towards a center of the ratchet recess 1508.

The ratchet wheel 1510 is removably disposed in the ratchet recess 1508. The ratchet wheel 1510 includes one or more pawls configured to engage the teeth and allow the ratchet wheel 1510 to rotate in one direction while preventing rotation in the opposite direction. The ratchet wheel 1510 also includes an aperture 1516 including a ledge extending substantially circumferentially around the aperture and extending radially inward toward a center of the aperture 1516. The ratchet wheel attachment utilizes a cut-out or groove area configured to receive a protrusion of a boss 1518. The boss 1518 extends in an upward direction from a central portion of the ratchet recess 1508 and includes the protrusion 1520 proximal to a top edge of the boss 1518 that extends radially outward from a center of the boss 1518. This protrusion and groove arrangement allows for the wheel 1510 to be put into place and then held in the well. Once the wheel is advanced, then the protrusion is captured, holding the ratchet wheel 1510 in the wheel well, yet readily removable from the ratchet recess 1508 if necessary by later realigning the protrusion and groove.

To facilitate ease of assembly and disassembly, the ratchet wheel 1510 may include an indicator 1522 and the device plate may include a corresponding indicator 1524, that when aligned indicate that the cut-out is aligned with the protrusion 1520. This allows a user to visually identify the correct position of the ratchet wheel 1510 to install or remove the ratchet wheel 1510.

The ratchet wheel 1510 also includes a locking element capture receptacle 1526 and an annular channel. The locking element capture receptacle 1526 is configured to receive an end of a locking element 1528 (similar to locking element 1328 illustrated in FIG. 33). The channel is configured to receive and allow the locking element 1528 to be coiled around the ratchet wheel 1510 to tighten the locking element 1528.

The ratchet wheel 1510 may also include one or more tool engaging features, illustrated as oblong apertures. The tool engaging features are configured to receive a corresponding male feature of a tool for use in rotating the ratchet wheel 1510 to coil the locking element 1528 around the ratchet wheel 1510.

The device 1500 includes a cut-out or area of reduced wall height 1530 proximal to the face. This allows the locking element 1528 to extend from the device 1500 and be coupled to the second device 1600, as described in further detail hereinafter.

The device 1500 may include one or more shear pin receiving receptacles (not shown but similar to receptacles 1332 illustrated in FIG. 32) in the face. The receiving receptacles are configured to receive corresponding shear pins 1634 extending from the second device 1600. This assists in aligning the device 1500 and the device 1600 when installed and used.

The device 1500 may also include one or more threaded fastener apertures 1536 configured to receive corresponding fasteners to couple the device 1500 to a bone or other body part. The threaded fastener apertures 1536 include a first aperture positioned proximal to the first end, a second aperture positioned proximal to the second end, and a third aperture in the boss 1518. The first and second apertures are offset with respect to the third aperture. The three apertures together form a triangular shape, with the third aperture being closest to the second device 1600 when installed.

The second device 1600 is configured to be positioned facing the first face of the device 1500 in an opposed relationship. As illustrated, the second device 1600 includes a first arm portion 1602 and a second arm portion 1604 connected together by a support portion 1610. When installed on a sternum, referring to FIG. 35, the first arm portion 1602 is positioned on a first portion 1704 of the separated sternum 1700 and the second arm portion 1604 is positioned on a second portion 1706 of the separated sternum 1700 with the support portion 1610 extending across the incision 1702.

The first and second arm portions 1602, 1604 each include one or more fastener apertures 1612 that receive fasteners to fasten the respective first and second arm portions 1602 and 1604 respectively to the first and second portions 1704, 1706 of the separated sternum 1700.

The second device 1600 also includes a locking element capture channel 1606 formed in a top of the second device 1600 and extending across the support portion 1610. The locking element capture channel 1606 is configured to receive an end of the locking element 1528. The locking element capture channel 1606 may also include a stop or ledge 1608 configured to prevent the locking element 1528 from being pulled out of the channel in a direction of the face.

When the devices 1500 and 1600 are installed, the device 1500 is fastened to a third portion 1708 of the separated sternum 1700; and the second device 1600 is fastened, wherein the respective first and second arm portions 1602 and 1604 are fastened to the first and second portions 1704, 1706 of the separated sternum 1700. To close the sternum 1700, the locking element 1528 is installed (which extends across the incision 1702) and the ratchet wheel 1510 is rotated. The locking element 1528 is coiled around the ratchet wheel 1510 to urge the device 1500 and second device 1600 together and into alignment with one another to close the sternum 1700 and align the portions of the sternum 1700 for healing. It should be appreciated that the devices 1500 and 1600 may be installed prior to or after separation of the sternum 1700.

It should be appreciated that the kind of foregoing embodiments that have cooperating pieces can be employed with a variety of integrated pieces. Those embodiments may have one member attached pre-resection (prior to separation), or a member attached on each side of what will be the resection, which are then joined, or rejoined in certain stances, together post-resection (after separation).

For example, any of the devices described herein may be placed or fastened in place pre-resection (prior to a cut or separation is made). The resection may then be made optionally using a surface or edge of the device as a guide to make the resection. An appropriate procedure may then be performed, and the device used to bring the separated portions of the bone, or other body parts back together into alignment with one another for healing.

Any number of markers, pins, and other markings or devices may be used and placed pre-resection to identify the original location of alignment of the bone or other body part pre-resection. These markers, pins, and other markings or devices may also be used to being the separated portions of the bone or other body part back together and into alignment for healing after the appropriate procedure has been performed (such as a surgical procedure).

While a plate or plate like member is described as positioned and/or an anchor element is applied to fix the plate in place, the plates and/or anchor elements may be placed in any order. Further, it should be appreciated that the features of one of the embodiments may be incorporated into the other embodiments, and/or the embodiments may be utilized together or in combination.

The embodiments described herein can be pre-contoured to fit anatomy either by offering numerous sizes and radii or by preoperatively imaging the patient's anatomy and building the implants from essentially three dimensional imaging.

Although the devices, systems, and methods have been described and illustrated in connection with certain embodiments, many variations and modifications should be evident to those skilled in the art and may be made without departing from the spirit and scope of the disclosure. For example, the components described herein may be made of titanium or other material suitable for surgical procedures. Other materials may also be used depending on the application of use. Similarly, the shapes, sizes, and dimensions of the components may be scaled up or down or altered to suit a particular application. The discourse is thus not to be limited to the precise details of methodology or construction set forth above as such variations and modification are intended to be included within the scope of the disclosure.

What is claimed is:

1. An implantable fixation device, comprising:
   a longitudinal first portion extending in a first longitudinal direction along the implantable fixation device, the longitudinal first portion including a plurality of first apertures situated along a first longitudinal axis in the implantable fixation device;
   a second portion extending from a first end of the longitudinal first portion, the second portion including at least a second aperture that is laterally offset from the first longitudinal axis in the implantable fixation device;
   a third portion extending from a second end of the longitudinal first portion, the third portion including at least a third aperture that is laterally offset from the first longitudinal axis in the implantable fixation device; and
   a longitudinal fourth portion, the longitudinal fourth portion extending alongside the longitudinal first portion in the first longitudinal direction but separated laterally from the longitudinal first portion by at least a first longitudinal channel and a second longitudinal channel that each have a maximum width that is less than a minimum width of the longitudinal first portion, the first longitudinal channel and the second longitudinal channel extending in the first longitudinal direction and separated from one another by a first connecting portion that extends laterally between the longitudinal first portion and the longitudinal fourth portion to connect the longitudinal first portion to the longitudinal fourth portion, the longitudinal fourth portion including at least a fourth aperture therein.

2. The implantable fixation device of claim 1, wherein the second portion and the third portion extend in opposite directions from the longitudinal first portion.

3. The implantable fixation device of claim 1, wherein the fourth aperture is laterally offset from the first longitudinal axis in the implantable fixation device.

4. The implantable fixation device of claim 1, wherein the longitudinal fourth portion includes a plurality of fourth apertures situated along a second longitudinal axis in the implantable fixation device.

5. The implantable fixation device of claim 4, wherein the first longitudinal axis and the second longitudinal axis run generally parallel to one another in the implantable fixation device.

6. The implantable fixation device of claim 5, wherein the second aperture and the third aperture are located between the first longitudinal axis and the second longitudinal axis in the implantable fixation device.

7. The implantable fixation device of claim 1 further comprising a third longitudinal channel extending in the first longitudinal direction, the third longitudinal channel separated from the second longitudinal channel by a second connecting portion that extends laterally between the longitudinal first portion and the longitudinal fourth portion to connect the longitudinal first portion to the longitudinal fourth portion.

8. The implantable fixation device of claim 1, wherein the longitudinal fourth portion is oriented longitudinally substantially between the second portion and the third portion.

9. The implantable fixation device of claim 1, wherein, in the first longitudinal direction, the entirety of the longitudinal fourth portion is located between the first end and the second end of the longitudinal first portion.

10. The implantable fixation device of claim 1, wherein the first longitudinal channel and the second longitudinal channel each have straight side edges extending in the first longitudinal direction.

11. The implantable fixation device of claim 1, wherein the second aperture and the third aperture are laterally offset generally to the same degree from the first longitudinal axis in the implantable fixation device.

12. The implantable fixation device of claim 1 in the form of a plate.

13. The implantable fixation device of claim 1, wherein respective edges of the longitudinal first portion, the second portion, and the third portion form a U-shape in the implantable fixation device.

14. The implantable fixation device of claim 1, wherein the first longitudinal channel includes an open first end.

15. The implantable fixation device of claim 1, wherein the second longitudinal channel includes a closed first end and a closed second end such that, along a top surface of the implantable fixation device, the second longitudinal channel is fully surrounded by material of the implantable fixation device.

16. An implantable fixation device, comprising:
    a longitudinal first portion extending in a first longitudinal direction along the implantable fixation device, the longitudinal first portion including a plurality of first apertures situated along a first longitudinal axis in the implantable fixation device;
    a second portion extending from a first end of the longitudinal first portion, the second portion including at least a second aperture that is laterally offset from the first longitudinal axis in the implantable fixation device;
    a third portion extending from a second end of the longitudinal first portion, the third portion including at least a third aperture that is laterally offset from the first longitudinal axis in the implantable fixation device; and
    a longitudinal fourth portion, the longitudinal fourth portion extending alongside the longitudinal first portion in the first longitudinal direction but separated laterally from the longitudinal first portion by at least a first longitudinal channel and a second longitudinal channel, the first longitudinal channel and the second longitudinal channel extending in the first longitudinal direction and separated from one another by a first connecting portion that extends laterally between the longitudinal first portion and the longitudinal fourth portion to connect the longitudinal first portion to the longitudinal fourth portion, the longitudinal fourth portion including a plurality of fourth apertures situated along a second longitudinal axis in the implantable fixation device, wherein the first longitudinal axis and the second longitudinal axis run generally parallel to one another in the implantable fixation device, and wherein the second aperture and the third aperture are located between the first longitudinal axis and the second longitudinal axis in the implantable fixation device.

17. An implantable fixation device, comprising:
    a longitudinal first portion extending in a first longitudinal direction along the implantable fixation device, the longitudinal first portion including a plurality of first apertures situated along a first longitudinal axis in the implantable fixation device;

a second portion extending from a first end of the longitudinal first portion, the second portion including at least a second aperture that is laterally offset from the first longitudinal axis in the implantable fixation device;

a third portion extending from a second end of the longitudinal first portion, the third portion including at least a third aperture that is laterally offset from the first longitudinal axis in the implantable fixation device;

a longitudinal fourth portion including at least a fourth aperture therein, the longitudinal fourth portion extending alongside the longitudinal first portion in the first longitudinal direction but separated laterally from the longitudinal first portion by at least a first longitudinal channel that extends in the first longitudinal direction and has a maximum width that is less than a minimum width of the longitudinal first portion; and a first connecting portion that extends laterally between the longitudinal first portion and the longitudinal fourth portion to connect the longitudinal first portion to the longitudinal fourth portion.

18. The implantable fixation device of claim 17, wherein the first connecting portion defines a closed first end of the first longitudinal channel.

19. The implantable fixation device of claim 18 further including a second connecting portion that extends laterally between the longitudinal first portion and the longitudinal fourth portion to connect the longitudinal first portion to the longitudinal fourth portion, the second connecting portion defining a closed second end of the first longitudinal channel.

20. The implantable fixation device of claim 17, wherein the first longitudinal channel includes a first longitudinal side edge and a second longitudinal side edge that extend generally parallel to one another in the first longitudinal direction.

\* \* \* \* \*